US012797079B2

(12) United States Patent
Dasi et al.

(10) Patent No.: US 12,797,079 B2
(45) Date of Patent: Nov. 17, 2026

(54) IMPLANTABLE VASCULAR SHUNT WITH REAL-TIME PRECISE FLOW CONTROL

(71) Applicants: GEORGIA TECH RESEARCH CORPORATION, Atlanta, GA (US); CHILDREN'S HEALTHCARE OF ATLANTA, INC., Atlanta, GA (US); EMORY UNIVERSITY, Atlanta, GA (US)

(72) Inventors: Lakshmi Prasad Dasi, Dublin, OH (US); Hoda Hatoum, Hancock, MI (US); Kevin Maher, Atlanta, GA (US); Milad Samaee, Marietta, GA (US); Subhadra Shashidharan, Atlanta, GA (US)

(73) Assignees: GEORGIA TECH RESEARCH CORPORATION, Atlanta, GA (US); CHILDREN'S HEALTHCARE OF ATLANTA, INC., Atlanta, GA (US); EMORY UNIVERSITY, Atlanta, GA (US)

( * ) Notice: Subject to any disclaimer, the term of this patent is extended or adjusted under 35 U.S.C. 154(b) by 43 days.

(21) Appl. No.: 18/571,436

(22) PCT Filed: Jun. 16, 2022

(86) PCT No.: PCT/US2022/033864

§ 371 (c)(1),
(2) Date: Dec. 18, 2023

(87) PCT Pub. No.: WO2022/266371

PCT Pub. Date: Dec. 22, 2022

(65) Prior Publication Data

US 2024/0225662 A1 Jul. 11, 2024

Related U.S. Application Data

(60) Provisional application No. 63/211,367, filed on Jun. 16, 2021.

(51) Int. Cl.
*A61B 17/135* (2006.01)
*A61B 17/11* (2006.01)
*A61B 17/00* (2006.01)

(52) U.S. Cl.
CPC .......... *A61B 17/1355* (2013.01); *A61B 17/11* (2013.01); *A61B 2017/00044* (2013.01);
(Continued)

(58) Field of Classification Search
CPC ... A61B 17/1355; A61B 17/132; A61B 17/12; A61B 17/122; A61B 2017/1139; A61B 2017/00778
See application file for complete search history.

(56) References Cited

U.S. PATENT DOCUMENTS 3,942,228 A 3/1976 Buckman et al.
4,643,389 A 2/1987 Elson et al.
(Continued)

OTHER PUBLICATIONS

Kiran, U., et al., The blalock and taussig shunt revisited. 2017. 20(3): p. 323.
(Continued)

*Primary Examiner* — Christina C Lauer
(74) *Attorney, Agent, or Firm* — Meunier Carlin & Curfman LLC

(57) ABSTRACT

A passive implantable medical device for controlling a flow of fluid through a tube within a patient includes a first component and a second component movably coupled to one another and defining a central passage configured for receiving a portion of the tube therethrough. The passive implantable medical device is configured for moving between a first configuration and a second configuration to constrict a portion of the tube. An active implantable medical device for controlling a flow of a first fluid through a tubing includes a flow control cuff comprising a stiff outer wall and a deformable inner wall which defines a central
(Continued)

opening sized such that the tubing can extend therethrough. A pump is configured to modulate a pressure of the second fluid within the interior space to apply a constrictive force to a section of the tubing.

18 Claims, 18 Drawing Sheets

(52) U.S. Cl.
CPC ............... *A61B 2017/00539* (2013.01); *A61B 2017/00557* (2013.01); *A61B 2017/00867* (2013.01); *A61B 2017/1139* (2013.01)

(56) References Cited

U.S. PATENT DOCUMENTS

| | | | | |
|---|---|---|---|---|
| 5,445,600 | A | 8/1995 | Abdulla | |
| 7,128,750 | B1 | 10/2006 | Stergiopulos | |
| 7,476,195 | B2 | 1/2009 | Sayet et al. | |
| 7,628,768 | B2 | 12/2009 | Faul et al. | |
| 7,722,662 | B2 * | 5/2010 | Steinke | A61F 2/94 623/1.15 |
| 7,967,769 | B2 | 6/2011 | Faul et al. | |
| 8,048,016 | B2 | 11/2011 | Faul et al. | |
| 8,079,974 | B2 | 12/2011 | Stergiopulos | |
| 8,506,517 | B2 | 8/2013 | Stergiopulos | |
| 8,517,970 | B2 | 8/2013 | Mathias et al. | |
| 8,551,032 | B2 | 10/2013 | Faul et al. | |
| 8,821,430 | B2 | 9/2014 | Stergiopulos | |
| 8,932,247 | B2 | 1/2015 | Stergiopulos | |
| 2006/0020324 | A1 * | 1/2006 | Schmid | A61F 2/856 623/1.16 |
| 2007/0032807 | A1 * | 2/2007 | Ortiz | A61B 17/122 606/153 |
| 2013/0178784 | A1 | 7/2013 | McNamara et al. | |
| 2017/0076874 | A1 | 3/2017 | O'Phelan et al. | |

OTHER PUBLICATIONS

Odim, J., et al., Sternotomy approach for the modified Blalock-Taussig shunt. Circulation, 1995. 92(9 Suppl): p. II256-61 https://www.ahajournals.org/doi/epub/10.1161/01.CIR.92.9.256.

Dirks, V., et al., Modified Blalock Taussig shunt: a not-so-simple palliative procedure. 2013. 44(6): p. 1096-1102.

Küçük, M., et al., Risk factors for thrombosis, overshunting and death in infants after modified Blalock-Taussig shunt. 2016. 32(3): p. 337.

Ramaswamy, P., et al., Systemic to pulmonary artery shunting for palliation. 2010.

Chikada, M., et al., Dilatable banding of a Blalock-Taussig shunt. 2002. 74(1): p. 253-255.

Honjo, O., C.J.O.T.i.T. Haller, and C. Surgery, Banding a Systemic-to-Pulmonary Shunt to Balance Pulmonary Blood Flow. 2017. 22(3): p. 157-172.

Douglas, W.I., et al., The adjustable systemic-pulmonary artery shunt provides precise control of flow in vivo. 2010. 56(1): p. 73-76.

International Search Report and Written Opinion received in PCT/US2022/033864 mailed Nov. 3, 2022.

* cited by examiner

IMPLANTABLE VASCULAR SHUNT WITH REAL-TIME PRECISE FLOW CONTROL

CROSS-REFERENCE TO RELATED APPLICATIONS

This application is a U.S. National Stage application filed under 35 U.S.C. § 371 of PCT/US2022/033864, filed Jun. 16, 2022, which claims the benefit of, and priority to, U.S. Provisional Application No. 63/211,367, filed Jun. 16, 2021, both of which are incorporated herein by reference in their entireties.

TECHNICAL FIELD

The present disclosure relates generally to implantable medical devices and, more specifically, to implantable medical devices for controlling a flow of fluid (e.g., blood) through vessels, tubes.

BACKGROUND

An aortic-to-pulmonary shunt is an example of a medical tubing that is implanted into a patient. More commonly, aortic-to-pulmonary shunts are referred to as systemic-to-pulmonary artery shunts or Blalock-Tausig shunts (also, Blalock-Thomas-Taussig shunts (BTTS)). A modified Blalock-Tausig shunt (mBTS), for example, is an aortic to pulmonary shunt which is implanted as part of a palliative procedure for cyanotic pediatric patients with a single ventricle and certain two ventricle palliation as a source of pulmonary blood flow (PBF). Although congenital heart disease surgery outcomes have improved, the mortality rate is still remarkable in the acute postoperative phase due to excessive PBF through the shunt and lack systemic circulation. Excessive pulmonary blood flow through the shunt can decrease systemic circulation, while the over-circulation to the lungs, known as run-off during diastole, causes low coronary perfusion.

While a smaller shunt size can reduce run-off, it will also reduce the overall flow to the lungs. Ideally, the shunt should allow more flow to the lungs when the heart is pumping and prevent run-off by increasing resistance to flow during the diastolic phase of the cardiac cycle. Moreover, it is also desired to restrict excessive blood flow to the lungs if systemic blood pressure increases. The manipulation of the pulmonary to systemic flow ratio ($Q_p/Q_s$) has been a topic of increasing interest; however, a practical approach to tackling this problem clinically has not been developed.

SUMMARY

One implementation of the present disclosure is an implantable medical device for controlling a flow of fluid through a tube within a patient. The implantable medical device includes a first component and a second component movably coupled to one another and defining a central passage extending along a central axis of the implantable medical device from a proximal end to a distal end thereof, where the central passage is configured for receiving a portion of the tube therethrough, and where the first component and the second component each include a proximal clamp portion configured for engaging a proximal portion of the tube; and a distal clamp portion configured for engaging a distal portion of the tube. In some embodiments, the implantable medical device is configured for moving between a first configuration and a second configuration, where the proximal clamp portions move away from one another and the distal clamp portions move toward one another when the implantable medical device moves from the first configuration to the second configuration.

Another implementation of the present disclosure is a method of using an implantable medical device for controlling a flow of fluid through a tube within a patient. The method includes engaging a proximal portion of the tube with a plurality of proximal clamp portions of the implantable medical device; engaging a distal portion of the tube with a plurality of distal clamp portions of the implantable medical device; and allowing the implantable medical device to move between a first configuration and a second configuration, where the proximal clamp portions move away from one another and the distal clamp portions move toward one another when the implantable medical device moves from the first configuration to the second configuration.

Yet another implementation of the present disclosure is an implantable medical device for controlling a flow of a first fluid through a tubing. The implantable medical device includes a flow control cuff comprising a stiff outer wall and a deformable inner wall which defines a central opening that extends along a central axis of the flow control cuff, where the central opening is sized such that the tubing can extend therethrough, and where the stiff outer wall and the deformable inner wall form an interior space that is filled with a second fluid; a pump configured to modulate a pressure of the second fluid within the interior space, where the deformable inner wall expands toward the central axis when the pressure of the second fluid is increased to apply a constrictive force to a section of the tubing; and a controller configured to control the flow of the first fluid through the tubing by selectively activating the pump to temporarily increase the pressure of the second fluid in the interior space, thereby selectively expanding the deformable inner wall of the flow control cuff.

Yet another implementation of the present disclosure is a method that includes providing a flow control device to be implanted on an atrio-pulmonary shunt in a patient, the flow control device comprising an implantable cuff having a stiff outer wall and a deformable inner wall which defines a central opening that extends along a central axis of the flow control cuff, where the central opening is sized such that the atrio-pulmonary shunt can extend therethrough, and where the stiff outer wall and the deformable inner wall for an interior space is filled with a fluid; recording, by a controller, electrocardiogram (EKG) signals to detect timing of diastole and systole in a patient's cardiac cycle; and based on the timing of diastole and systole in the patient's cardiac cycle activating, by the controller, a pump to increase a pressure of the fluid within the interior space responsive to the cardiac cycle entering a diastole period, where the increase in the pressure causes the deformable inner wall of the implantable cuff to expand from a first diameter to second diameter to apply a constrictive force to a section of the atrio-pulmonary shunt; or deactivating or reversing, by the controller, the pump to decrease the pressure of the fluid within the interior space responsive to the cardiac cycle entering a systole period, where the decrease in the pressure causes the deformable inner wall of the implantable cuff to contract from the second diameter to the first diameter to remove the constrictive force to the section of the atrio-pulmonary shunt.

Yet another implementation of the present disclosure is a system that includes an implantable cuff comprising a stiff outer wall and a deformable inner wall which defines a central opening that extends along a central axis of the implantable cuff, where the central opening is sized such that an atrio-pulmonary shunt can extend therethrough, and where the stiff outer wall and the deformable inner wall for an interior space is filled with a fluid; a pump configured to modulate a pressure of the fluid within the interior space to selectively expand the deformable inner wall from a first diameter to a second diameter, where the first diameter is larger than the second diameter such that the deformable inner wall expands toward the central axis to apply a constrictive force to a section of the atrio-pulmonary shunt when the deformable inner wall is expanded to the second diameter; and a controller configured to control the flow of the fluid through the atrio-pulmonary shunt by selectively activating the pump to cause the deformable inner wall to expand from the first diameter to the second diameter or contract from the second diameter to the first diameter.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

DETAILED DESCRIPTION

Figure 1:
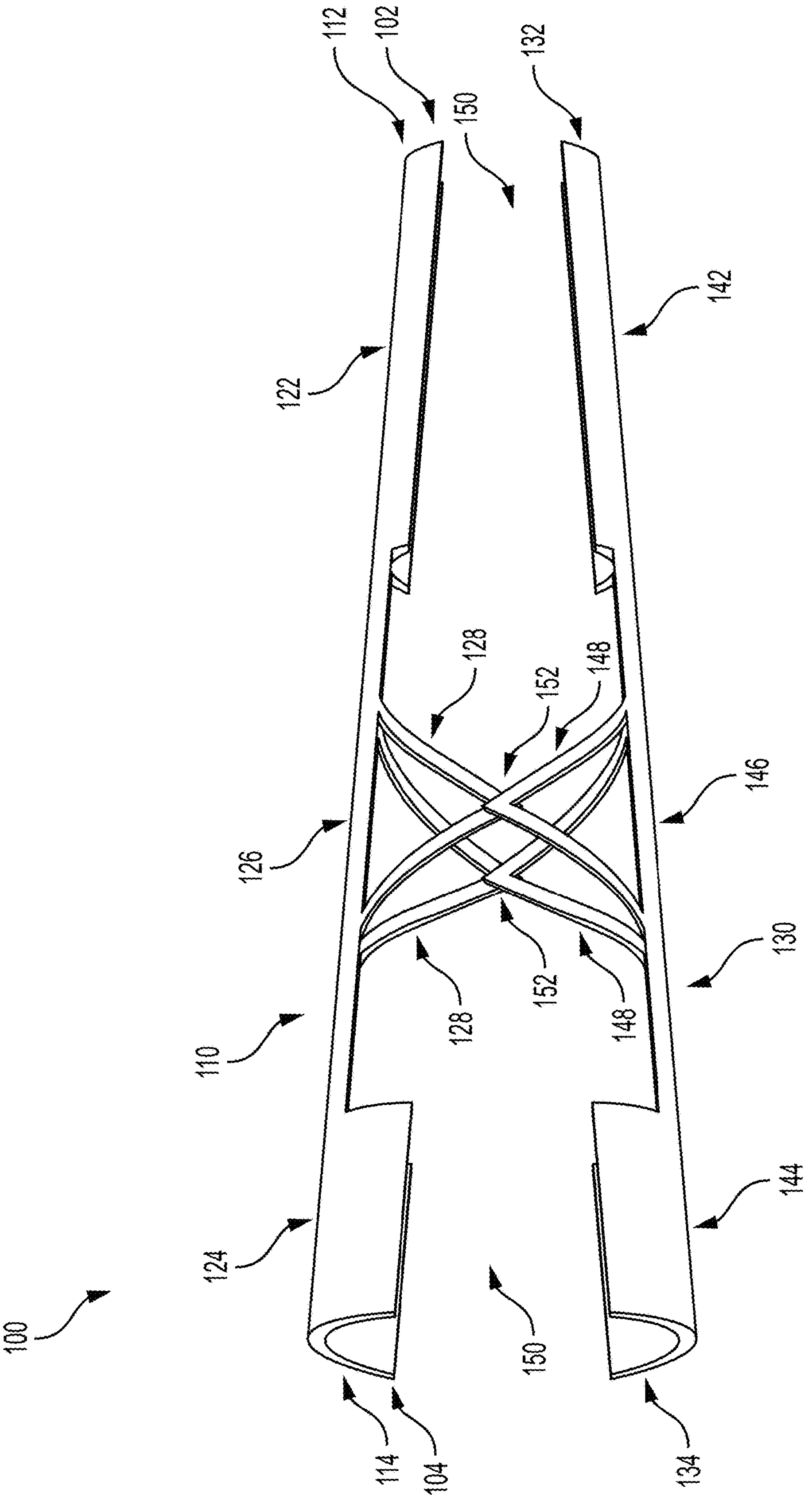
FIG. 1 is a perspective view of a passive flow control device, according to some embodiments, showing the passive flow control device in a first configuration.

Referring generally to the figures, implantable medical devices for controlling the flow of fluid (e.g., blood) through vessels, tubes, etc., within a patient are shown, accordingly to various embodiments. In particular, both a passive flow control device and an active flow control device are shown. The passive control device may include two or more components that are movably coupled and that define a central axis through which a tubing (e.g., a Blalock-Thomas-Taussig shunt (BTTS) or mBTS) can extend. Each of the first and second components may include a proximal and distal clamp portions that respectively engage proximal and distal portions of the tube. In particular, the passive control device, which notably does not require an external power source to operate, can move among a number of configurations, including between a first and second configuration to selectively constrict portions of the tubing.

The active flow control device may include an implantable cuff (e.g., a cylindrical, torus, or ring-shaped expandable balloon) that can be positioned around a section of tubing (e.g., a BTTS) such that the tubing extends through an opening in the center of the implantable cuff. A micropump, which can also be implanted into the patient, may control expansion of an inner wall the implantable cuff. For example, the micropump may apply a hydraulic force to the implantable cuff (e.g., by pumping a fluid, such as saline, into the implantable cuff) which causes the inner wall of the implantable cuff to expand. As the inner wall expands, it constricts the section of tubing, thereby slowing the flow of fluid through the tubing (e.g., by reducing the amount of fluid that can flow through the section of tubing). In a similar manner, the micropump may reduce expansion of the implantable cuff by removing or reducing the hydraulic force, which reduces the construction on the section of tubing and allows a greater volume of fluid to flow through the tubing. Additionally, in some embodiments, the micropump can be configured to sync the expansion/deflation of the implantable cuff with contractions of the user's heart to further balance the pulmonary to systemic flow ratio ($Q_p/Q_s$) and reduce the occurrence of the various issues described above (e.g., lack of oxygenation, drops in diastolic pressure, etc.). In some embodiments, the active flow control device may operate with the components of the passive control device.

To these points, both the passive and active flow control devices described herein provide numerous advantages to both patients and physicians. For example, both the passive and active flow control devices provide the physician with greater control/adjustment of flow rates through a shunt or other tubing. Further, these devices can reduce the need for patients to undergo numerous surgeries for tube replacement, etc. For example, in a pediatric patient, a large diameter BTTS may be implanted initially, along with one of the devices described herein to control the flow rate of fluid through the shunt, which reduces or eliminates the need for the patient to have additional or recurring surgeries to replace an original shunt with one of a different size (e.g., increasing the shunt size as the patient grows).

The balance of systemic and pulmonary flows can facilitate the prevention of damage induced to the lungs and depriving the systemic circulation of the required blood flow. Unbalancing $Q_P/Q_S$ leads to a lack of oxygenation, a significant drop in diastolic pressure, and compromised coronary perfusion, possibly inducing a sudden cardiac death. Moreover, as the patient grows, the aortic pressure increases, leading to a subsequent increase in shunt flow and pulmonary and system flow balance loss. Additionally, it should be appreciated that the passive and active devices described herein may be used to control a flow of fluid through any type of tubing or vessel, biological or otherwise. For example, while generally described as being used on an BTTSs or other types of shunts, the passive and active flow control devices described herein may be used to control the flow of fluid through blood vessels, ureters, fallopian tubes, vas deferens, and the like. Additional features and advantages of the passive and active flow control devices will be described in greater detail below.

Passive Flow Control

Referring now to the drawings, FIGS. 1-4 show a passive flow control device 100, according to some embodiments. Device 100 is fully implantable within a patient, as described in detail below. As described herein, device 100 may be used for controlling a flow of fluid through a tube 160 within the patient. For example, device 100 may be used for controlling a flow of blood through tube 160. In some embodiments, tube 160 may be a vessel of the patient, and device 100 may be implanted for controlling a flow of blood through the vessel. In some embodiments, tube 160 may be formed of a biocompatible synthetic material and implanted within the patient. In such embodiments, tube 160 may be considered to be part of device 100. In some embodiments, tube 160 may be a shunt, such as an atrio-pulmonary shunt. In some embodiments, tube 160 may be a modified Blalock-Taussig shunt (mBTS) or Blalock-Thomas-Taussig shunt (BTTS).

Figure 4:
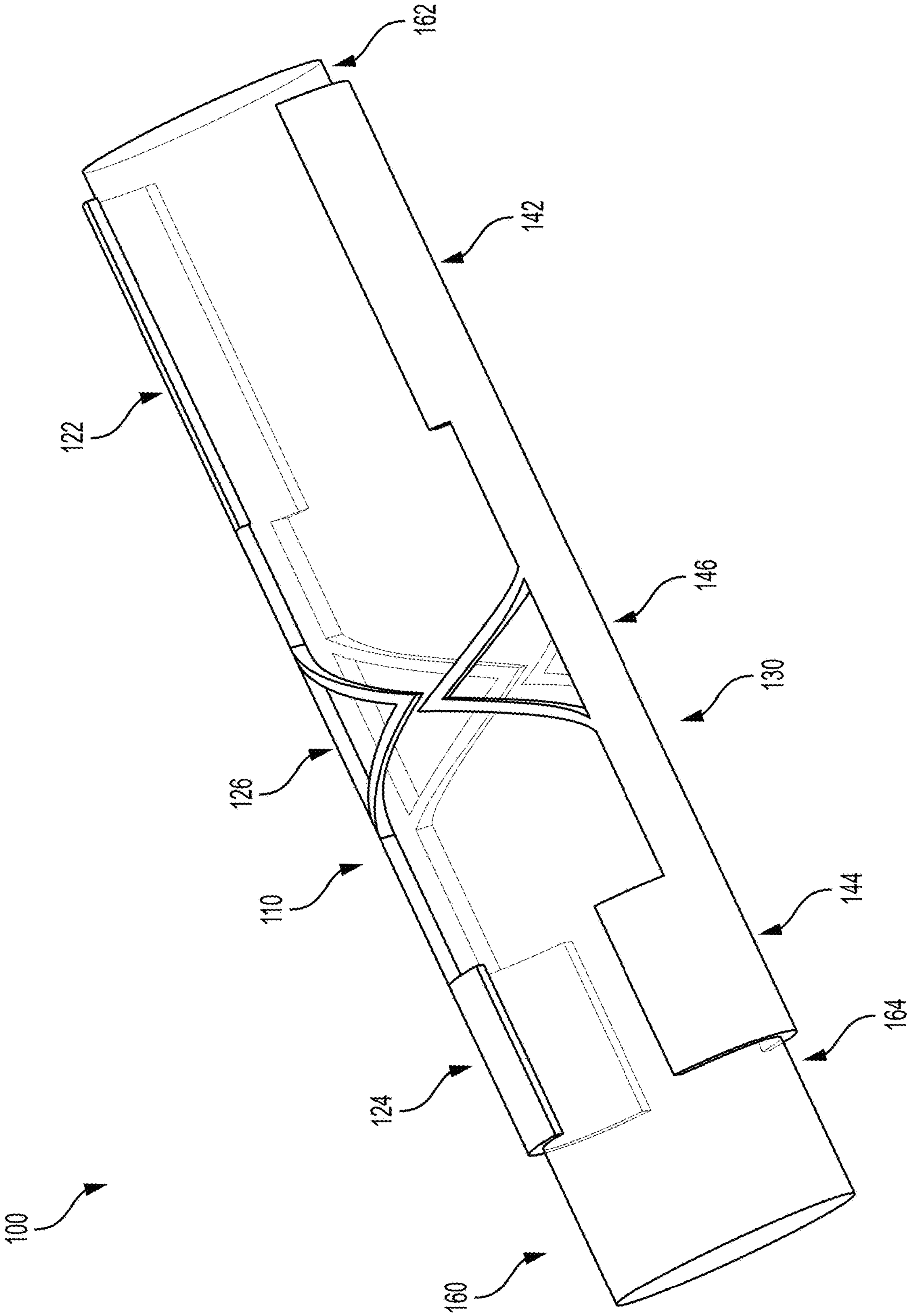
FIG. 4 is a perspective view of the passive flow control device of FIG. 1 positioned on a tube for controlling a flow of fluid through the tube.

The passive flow control device 100 may be formed as an elongate structure having a proximal end 102 and a distal end 104 disposed opposite one another in a direction of a central axis (i.e., a centered, longitudinal axis) of device 100. As shown, device 100 may include a first component 110 and a second component 130 movably coupled to one another. In this manner, device 100 may be configured for moving between a plurality of different configurations by relative movement of first component 110 and second component 130, as described below. As shown, first component 110 and second component 130 may define a central passage 150 therebetween. Central passage 150 may extend along the central axis of the device from the proximal end 102 to the distal end 104. Central passage 150 may be configured for receiving a portion of tube 160 therethrough. For example, as shown in FIG. 4, tube 160 may extend through central passage 150 such that first component 110 and second component 130 extend around (i.e., encircle) a portion of tube 160.

First component 110 may be formed as an elongate structure having a proximal end 112 and a distal end 114 disposed opposite one another in a direction of a longitudinal axis of first component 110. As shown, first component 110 may include a proximal clamp portion 122, a distal clamp portion 124, an intermediate portion 126, and a pair of hinge portions 128. In some embodiments, as shown, proximal clamp portion 122, distal clamp portion 124, intermediate portion 126, and hinge portions 128 may be integrally formed with one another. In other embodiments, two or more portions of first component 110 may be separately formed and fixedly coupled to one another. Proximal clamp portion 122 may be configured for engaging tube 160. In particular, proximal clamp portion 122 may be configured for engaging a proximal end portion 162 of tube 160, as shown in FIG. 4. Distal clamp portion 124 also may be configured for engaging tube 160. In particular, distal clamp portion 124 may be configured for engaging a distal end portion 164 of tube 160, as shown in FIG. 4. In some embodiments, as shown, each of proximal clamp portion 122 and distal clamp portion 124 may have a partial cylindrical shape, with a concave internal surface and a convex external surface. Various other shapes of proximal clamp portion 122 and distal clamp portion 124 may be used in other embodiments. In some embodiments, as shown, proximal clamp portion 122 and distal clamp portion 124 may have different lengths. For example, a length of proximal clamp portion 122 may be greater than or less than a length of distal clamp portion 124. In some embodiments, as shown, the internal surfaces of proximal clamp portion 122 and distal clamp portion 124 may have different surface areas. For example, a surface area of the internal surface of proximal clamp portion 122 may be greater than or less than a surface area of the internal surface of distal clamp portion 124. As shown, intermediate portion 126 may extend from proximal clamp portion 122 to distal clamp portion 124. Hinge portions 128 may be disposed between proximal clamp portion 122 and distal clamp portion 124 and extend from intermediate portion 126. As shown, hinge portions 128 may be disposed opposite one another along opposite sides of first component 110. In some embodiments, first component 110 may be formed of a shape memory material, such as nickel-titanium alloy, although other suitable materials may be used for first component 110 in other embodiments.

In a similar manner, second component 130 may be formed as an elongate structure having a proximal end 132 and a distal end 134 disposed opposite one another in a direction of a longitudinal axis of second component 130. In some embodiments, as shown, second component 130 may be formed as a mirror image of first component 110. As shown, second component 130 may include a proximal clamp portion 142, a distal clamp portion 144, an intermediate portion 146, and a pair of hinge portions 148. In some embodiments, as shown, proximal clamp portion 142, distal clamp portion 144, intermediate portion 146, and hinge portions 148 may be integrally formed with one another. In other embodiments, two or more portions of second component 130 may be separately formed and fixedly coupled to one another. The proximal clamp portion 134 may be configured for engaging tube 160. In particular, proximal clamp portion 142 may be configured for engaging the proximal end portion 162 of tube 160, as shown in FIG. 4. Distal clamp portion 144 also may be configured for engaging tube 160. In particular, distal clamp portion 144 may be configured for engaging the distal end portion 164 of tube 160, as shown in FIG. 4. In some embodiments, as shown, each of proximal clamp portion 142 and distal clamp portion 144 may have a partial cylindrical shape, with a concave internal surface and a convex external surface. Various other shapes of proximal clamp portion 142 and distal clamp portion 144 may be used in other embodiments. In some embodiments, as shown, proximal clamp portion 142 and distal clamp portion 144 may have different lengths. For example, a length of proximal clamp portion 142 may be greater than or less than a length of distal clamp portion 144. In some embodiments, as shown, the internal surfaces of proximal clamp portion 142 and distal clamp portion 144 may have different surface areas. For example, a surface area of the internal surface of proximal clamp portion 142 may be greater than or less than a surface area of the internal surface of distal clamp portion 144. As shown, intermediate portion 146 may extend from proximal clamp portion 142 to distal clamp portion 144. Hinge portions 148 may be disposed between proximal clamp portion 142 and distal clamp portion 144 and extend from intermediate portion 146. As shown, hinge portions 148 may be disposed opposite one another along opposite sides of second component 130. In some embodiments, second component 130 may be formed of a shape memory material, such as nickel-titanium alloy, although other suitable materials may be used for second component 130 in other embodiments.

As shown, first component 110 and second component 130 may be pivotally coupled to one another at a pair of hinges 152. In this manner, device 100 may be configured for moving between a plurality of different configurations by relative pivotal movement of first component 110 and second component 130 about hinges 152. In some embodiments, first component 110 and second component 130 may be pivotally coupled to one another at a pair of hinges 152 by one or more fasteners coupling the respective pairs of hinge portions 128, 148. Other means for pivotally coupling first component 110 and second component 130 may be used in other embodiments.

Figure 2:
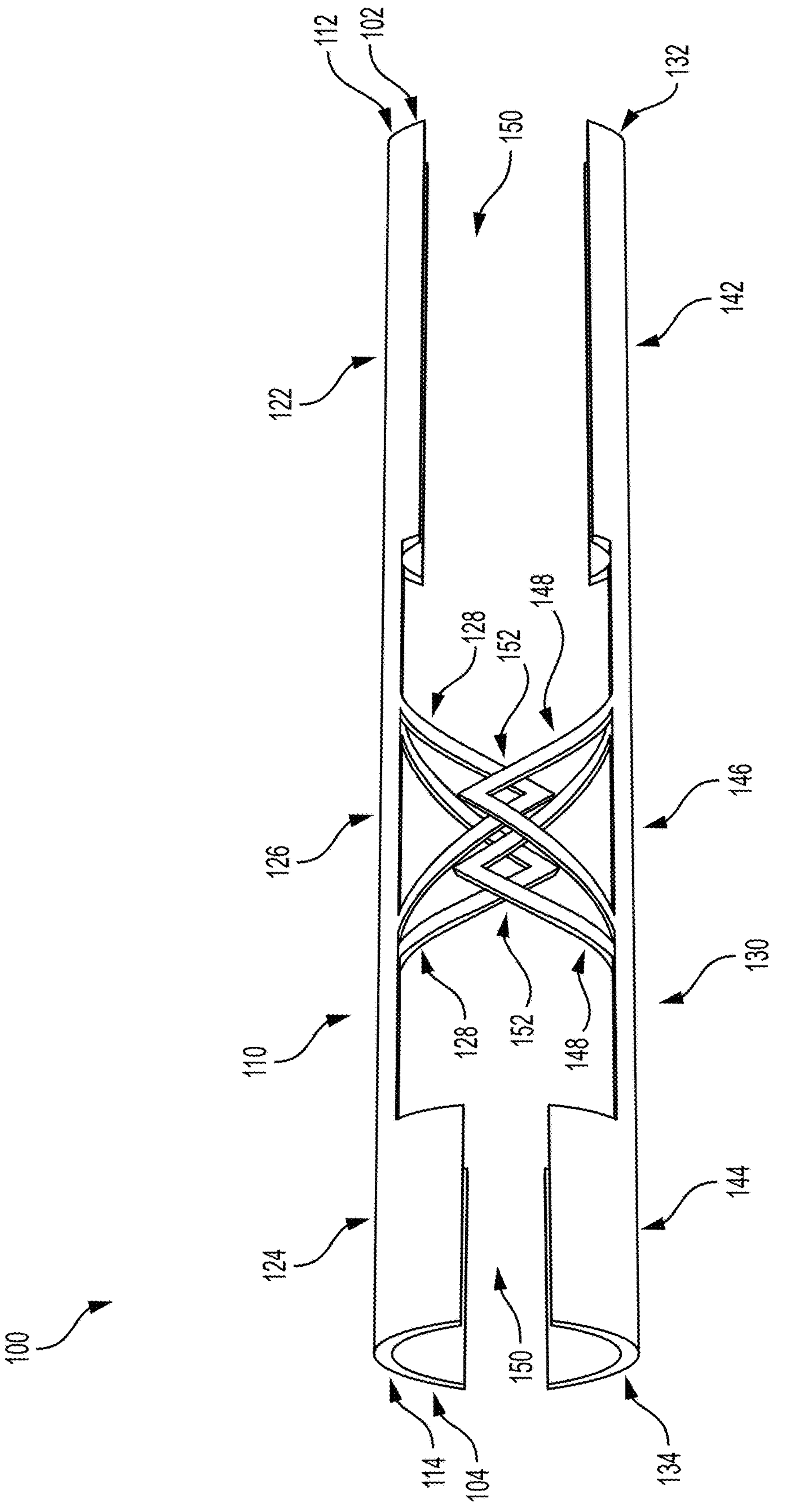
FIG. 2 is a perspective view of the passive flow control device of FIG. 1, showing the passive flow control device in a second configuration.
Figure 3:
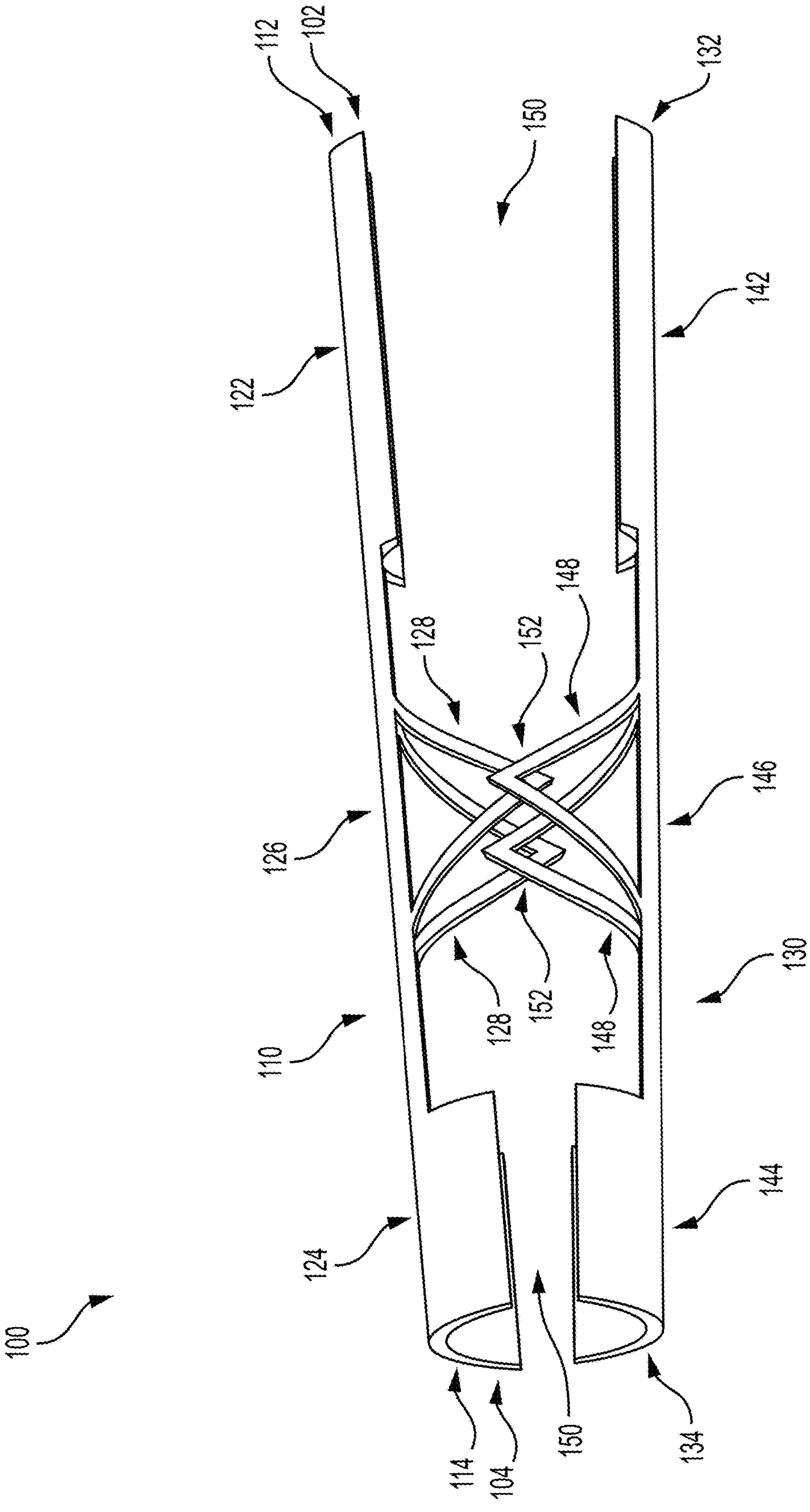
FIG. 3 is a perspective view of the passive flow control device of FIG. 1, showing the passive flow control device in a third configuration.

According to the illustrated embodiment, device 100 may be configured for moving between a first configuration, as shown in FIG. 1, a second configuration, as shown in FIG. 2, and a third configuration, as shown in FIG. 3. As shown, relative spacings between the proximal clamp portions 122, 142 and between the distal clamp portions 124, 144 may be varied as the device is moved between the different configurations. In this manner, the proximal clamp portions 122, 142 may be configured for constricting the proximal end portion 162 of tube 160, thereby restricting fluid flow through tube 160, when device 100 is in certain configurations and for not constricting the proximal end portion 162 when device 100 is in other configurations. In a similar manner, the distal clamp portions 124, 144 may be configured for constricting the distal end portion 164 of tube 160, thereby restricting fluid flow through tube 160, when device 100 is in certain configurations and for not constricting the distal end portion 164 when device 100 is in other configurations. In some embodiments, as shown, when device 100 is moved from the first configuration to the second configuration, the proximal clamp portions 122, 142 may move away from one another and the distal clamp portions 124, 144 may move toward one another. In contrast, when device 100 is moved from the second configuration to the first configuration, the proximal clamp portions 122, 142 may move toward one another and the distal clamp portions 124, 144 may move away from one another. In some embodiments, as shown, when device 100 is moved from the second configuration to the third configuration, the proximal clamp portions 122, 142 may move away from one another and the distal clamp portions 124, 144 may move toward one another. In contrast, when device 100 is moved from the third configuration to the second configuration, the proximal clamp portions 122, 142 may move toward one another and the distal clamp portions 124, 144 may move away from one another.

In some embodiments, device 100 may be biased to the first configuration. For example, first component 110 and second component 130 may be formed of a shape memory material and may have a shape memory of the first configuration. Additionally, or alternatively, device 100 may include a spring configured for interacting with first component 110 and second component 130 and biasing device 100 to the first configuration. In some embodiments, device 100 may be configured for moving from the first configuration to the second configuration when a pressure within the proximal portion 162 of tube 160 exceeds a first pressure threshold. In particular, the pressure within the proximal portion 162 may cause the proximal clamp portions 122, 124 to move away from one another. In some embodiments, device 100 may be configured for moving from the second configuration to the third configuration when the pressure within the proximal portion 162 exceeds a second pressure threshold that is greater than the first pressure threshold. In particular, the pressure within the proximal portion 162 may cause the proximal clamp portions 122, 124 to move further away from one another.

In some embodiments, the proximal clamp portions 122, 142 may be configured for constricting the proximal portion 162 of tube 160 when device 100 is in the first configuration, and the distal clamp portions 124, 144 may be configured for not constricting the distal portion 164 of tube 160 when device 100 is in the first configuration. In some embodiments, the proximal clamp portions 122, 142 may be configured for constricting the proximal portion 162 of tube 160 when device 100 is in the second configuration, and the distal clamp portions 124, 144 may be configured for not constricting the distal portion 164 of tube 160 when device 100 is in the second configuration. In other embodiments, the proximal clamp portions 122, 142 may be configured for constricting the proximal portion 162 of tube 160 when device 100 is in the second configuration, and the distal clamp portions 124, 144 may be configured for constricting the distal portion 164 of tube 160 when device 100 is in the second configuration. In other embodiments, the proximal clamp portions 122, 142 may be configured for not constricting the proximal portion 162 of tube 160 when device 100 is in the second configuration, and the distal clamp portions 124, 144 may be configured for constricting the distal portion 164 of tube 160 when device 100 is in the second configuration. In other embodiments, the proximal clamp portions 122, 142 may be configured for not constricting the proximal portion 162 of tube 160 when device 100 is in the second configuration, and the distal clamp portions 124, 144 may be configured for not constricting the distal portion 164 of tube 160 when device 100 is in the second configuration. In some embodiments, the proximal clamp portions 122, 142 may be configured for not constricting the proximal portion 162 of tube 160 when device 100 is in the third configuration, and the distal clamp portions 124, 144 may be configured for constricting the distal portion 164 of tube 160 when device 100 is in the third configuration.

In some embodiments, tube 160 may be formed of a biocompatible synthetic material and implanted within the patient. In such embodiments, tube 160 may be considered to be part of device 100. In some embodiments, tube 160 may be a shunt, such as an atrio-pulmonary shunt. In some embodiments, tube 160 may be an mBTS or BTTS. In some embodiments, first component 110 and second component 130 may extend around tube 160 such that the proximal clamp portions 122, 142 and the distal clamp portions 124, 144 engage the external surface of tube 160. In other embodiments, first component 110 and second component 130 may be embedded within the wall of the tube such that first component 110 and second component 130 are disposed between the external surface and the internal surface of tube 160.

Figure 5:
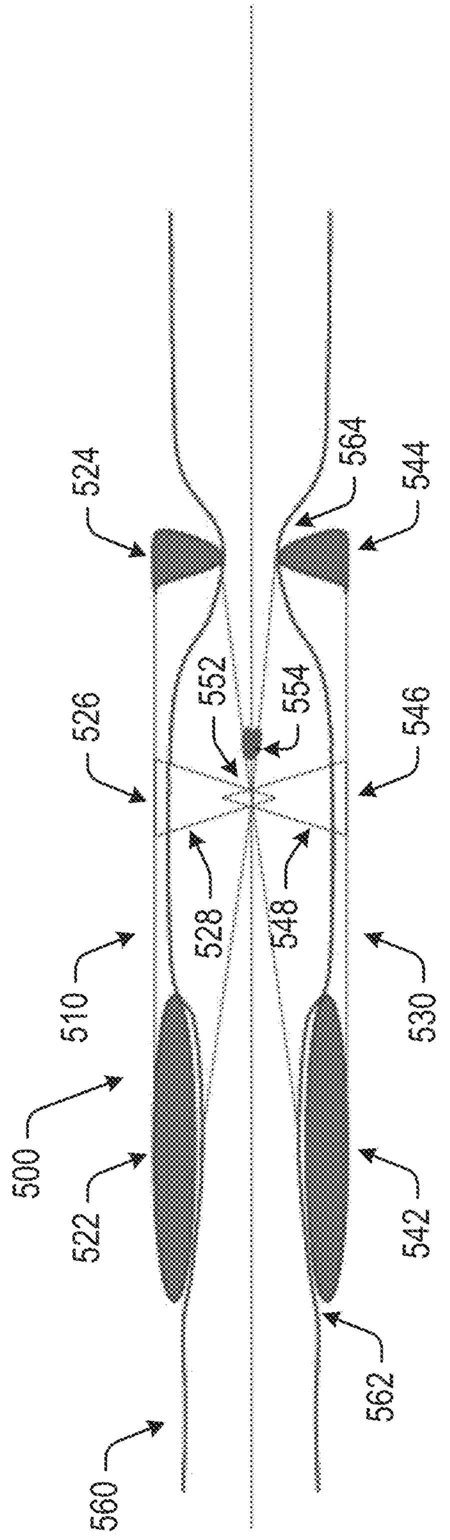
FIG. 5 is a schematic diagram of a passive flow control device positioned on a tube for controlling a flow of fluid through the tube, according to some embodiments.
Figure 6:
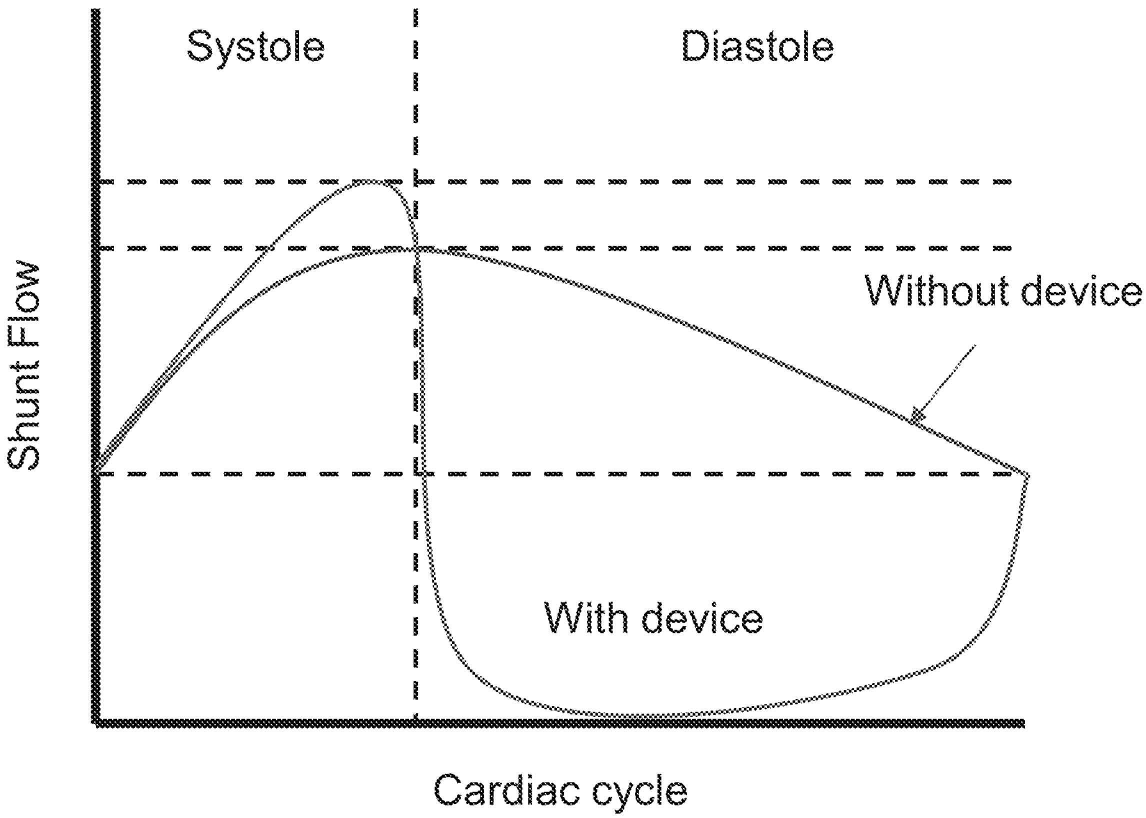
FIG. 6 is an example graph showing blood flow through a shunt with and without the passive flow control device of FIG. 1, according to some embodiments.

FIG. 5 schematically illustrates a passive flow control device 500 used for controlling a flow of fluid through a tube 560 within a patient, according to some embodiments. The passive flow control device 500 generally may be configured in a manner similar to the passive flow control device 100 described above. Certain similarities and differences between the flow control device 500 and the passive flow control device 100 will be appreciated from the drawings. The device 500 is fully implantable within a patient, as described in detail below. In some embodiments, the device 500 may be used for controlling a flow of blood through the tube 560. In some embodiments, the tube 560 may be a vessel of the patient, and the device 500 may be implanted for controlling a flow of blood through the vessel. In some embodiments, the tube 560 may be formed of a biocompatible synthetic material and implanted within the patient. In such embodiments, the tube 560 may be considered to be part of the device 500. In some embodiments, the tube 560 may be a shunt, such as an atrio-pulmonary shunt. In some embodiments, the tube 560 may be an mBTS or BTTS.

The passive flow control device 500 may be formed as an elongate structure having a proximal end 502 and a distal end 504 disposed opposite one another in a direction of a central axis (i.e., a centered, longitudinal axis) of the device 500. As shown, the device 500 may include a first component 510 and a second component 530 movably coupled to one another. In this manner, the device 500 may be configured for moving between a plurality of different configurations by relative movement of the first component 510 and the second component 530, as described below. As shown, the first component 510 and the second component 530 may define a central passage 550 therebetween. The central passage 550 may extend along the central axis of the device from the proximal end 502 to the distal end 504. The central passage 550 may be configured for receiving a portion of the tube 560 therethrough. For example, as shown in FIG. 5, the tube 560 may extend through the central passage 550 such that the first component 510 and the second component 530 extend around (i.e., encircle) a portion of the tube 560.

The first component 510 may be formed as an elongate structure having a proximal end 512 and a distal end 514 disposed opposite one another in a direction of a longitudinal axis of the first component 510. As shown, the first component 510 may include a proximal clamp portion 522, a distal clamp portion 524, an intermediate portion 526, and a pair of hinge portions 528. The proximal clamp portion 522 may be configured for engaging the tube 560. In particular, the proximal clamp portion 522 may be configured for engaging a proximal end portion 562 of the tube 560, as shown. The distal clamp portion 524 also may be configured for engaging the tube 560. In particular, the distal clamp portion 524 may be configured for engaging a distal end portion 564 of the tube 560, as shown. Various shapes of the proximal clamp portion 522 and the distal clamp portion 524 may be used. In some embodiments, as shown, the proximal clamp portion 522 and the distal clamp portion 524 may have different lengths. For example, a length of the proximal clamp portion 522 may be greater than or less than a length of the distal clamp portion 524. In some embodiments, as shown, the internal surfaces of the proximal clamp portion 522 and the distal clamp portion 524 may have different surface areas. For example, a surface area of the internal surface of the proximal clamp portion 522 may be greater than or less than a surface area of the internal surface of the distal clamp portion 524. As shown, the intermediate portion 526 may extend from the proximal clamp portion 522 to the distal clamp portion 524. The hinge portions 528 may be disposed between the proximal clamp portion 522 and the distal clamp portion 524 and extend from the intermediate portion 526. The hinge portions 528 may be disposed opposite one another along opposite sides of the first component 510. In some embodiments, the first component 510 may be formed of a shape memory material, such as nickel-titanium alloy, although other suitable materials may be used for the first component 510 in other embodiments.

In a similar manner, the second component 530 may be formed as an elongate structure having a proximal end 532 and a distal end 534 disposed opposite one another in a direction of a longitudinal axis of the second component 530. In some embodiments, as shown, the second component 530 may be formed as a mirror image of the first component 510. As shown, the second component 530 may include a proximal clamp portion 542, a distal clamp portion 544, an intermediate portion 546, and a pair of hinge portions 548. The proximal clamp portion 534 may be configured for engaging the tube 560. In particular, the proximal clamp portion 542 may be configured for engaging the proximal end portion 562 of the tube 560, as shown. The distal clamp portion 544 also may be configured for engaging the tube 560. In particular, the distal clamp portion 544 may be configured for engaging the distal end portion 564 of the tube 560, as shown. Various shapes of the proximal clamp portion 542 and the distal clamp portion 544 may be used. In some embodiments, as shown, the proximal clamp portion 542 and the distal clamp portion 544 may have different lengths. For example, a length of the proximal clamp portion 542 may be greater than or less than a length of the distal clamp portion 544. In some embodiments, as shown, the internal surfaces of the proximal clamp portion 542 and the distal clamp portion 544 may have different surface areas. For example, a surface area of the internal surface of the proximal clamp portion 542 may be greater than or less than a surface area of the internal surface of the distal clamp portion 544. As shown, the intermediate portion 546 may extend from the proximal clamp portion 542 to the distal clamp portion 544. The hinge portions 548 may be disposed between the proximal clamp portion 542 and the distal clamp portion 544 and extend from the intermediate portion 546. The hinge portions 548 may be disposed opposite one another along opposite sides of the second component 530. In some embodiments, the second component 530 may be formed of a shape memory material, such as nickel-titanium alloy, although other suitable materials may be used for the second component 530 in other embodiments.

The first component 510 and the second component 530 may be pivotally coupled to one another at a pair of hinges 552. In this manner, the device 500 may be configured for moving between a plurality of different configurations by relative pivotal movement of the first component 510 and the second component 530 about the hinges 552. In some embodiments, the first component 510 and the second component 530 may be pivotally coupled to one another at a pair of hinges 552 by one or more fasteners coupling the respective pairs of the hinge portions 528, 548. Other means for pivotally coupling the first component 510 and the second component 530 may be used in other embodiments. Relative spacings between the proximal clamp portions 522, 542 and between the distal clamp portions 524, 544 may be varied as the device is moved between the different configurations. In this manner, the proximal clamp portions 522, 542 may be configured for constricting the proximal end portion 562 of the tube 560, thereby restricting fluid flow through the tube 560, when the device 500 is in certain configurations and for not constricting the proximal end portion 562 when the device 500 is in other configurations. In a similar manner, the distal clamp portions 524, 544 may be configured for constricting the distal end portion 564 of the tube 560, thereby restricting fluid flow through the tube 560, when the device 500 is in certain configurations and for not constricting the distal end portion 564 when the device 500 is in other configurations. In some embodiments, as shown, the device 500 may include one or more spacers 554 configured for limiting movement of the device 500 from one configuration to another configuration. For example, the one or more spacers 554 may be configured for interacting with the first component 510 and the second component 530, such as the hinge portions 528, 548 thereof, to limit movement of the device 500 from one configuration to another configuration.

Active Flow Control

Figure 7:
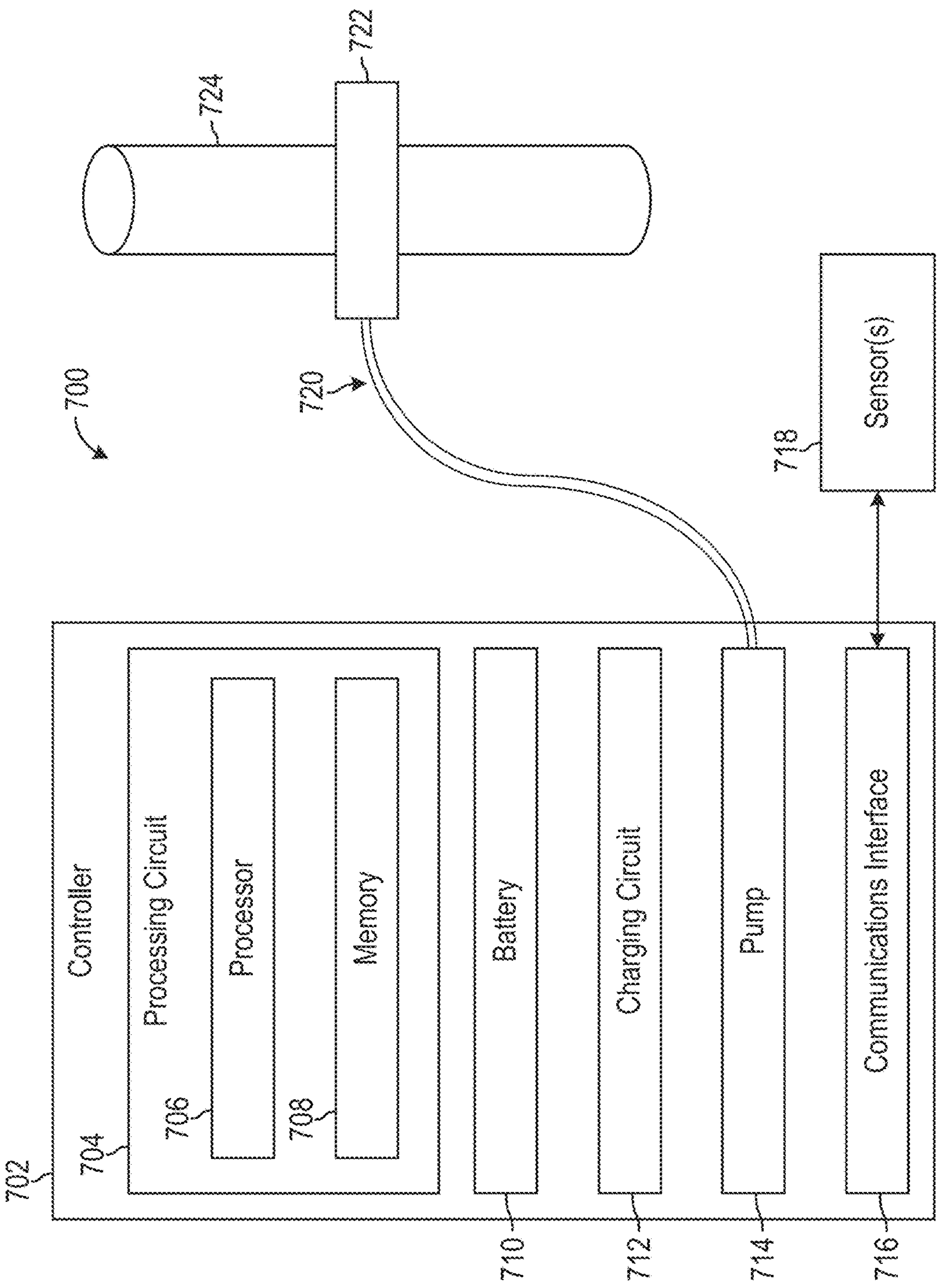
FIG. 7 is a block diagram of an active flow control system, according to some embodiments.

Referring now to FIG. 7, a block diagram of an active flow control system 700 is shown, according to some embodiments. As described herein, system 700 is generally fully implantable into a patient, as will be described in detail below. However, it should also be appreciated that any of the components of system 700 described herein may be positioned external (i.e., are not implanted) to the patient. Additionally, as with device 100 described above, system 700 is described herein for controlling the flow of fluid through an atrio-pulmonary (e.g., an mBTS or BTTS); however, it should be appreciated that system 700 may control the flow of fluid through any section of tubing, including but not limited to blood vessels, ureters, silicone or other medical-grade tubing, etc.

System 700 is shown to include a controller 702 configured that controls the flow of fluid (e.g., blood) through a tubing 724 by selectively constricting a section of tubing 724, as will be described in greater detail below. As described herein, tubing 724 may be any biological tubing including, but not limited to, blood vessels, ureters, fallopian tubes, vas deferens, and the like. Tubing 724 may also be any flexible, man-made, medical tubing, such as an atrio-pulmonary shunt (e.g., an mBTS). In one example, tubing 724 is a BTS or BTTS formed of polytetrafluoroethylene (PTFE) or another flexible material. For the same of simplicity, tubing 724 will generally be referred to herein as an atrio-pulmonary shunt. Accordingly, tubing 724 may the same as, or equivalent to, tubing 162 described above with respect to FIG. 4.

Controller 702 includes a processing circuit 704 that includes a processor 706 and a memory 708. Processor 706 can be a general-purpose processor, an application specific integrated circuit (ASIC), one or more field programmable gate arrays (FPGAs), a group of processing components, or other suitable electronic processing components. In some embodiments, processor 706 is configured to execute program code stored on memory 708 to cause controller 702 to perform one or more operations. Memory 708 can include one or more devices (e.g., memory units, memory devices, storage devices, etc.) for storing data and/or computer code for completing and/or facilitating the various processes described in the present disclosure.

In some embodiments, memory 708 includes tangible, computer-readable media that stores code or instructions executable by processor 706. Tangible, computer-readable media refers to any media that is capable of providing data that causes controller 702 (i.e., a machine) to operate in a particular fashion. Example tangible, computer-readable media may include, but is not limited to, volatile media, non-volatile media, removable media and non-removable media implemented in any method or technology for storage of information such as computer readable instructions, data structures, program modules or other data. Accordingly, memory 708 can include random access memory (RAM), read-only memory (ROM), hard drive storage, temporary storage, non-volatile memory, flash memory, optical memory, or any other suitable memory for storing software objects and/or computer instructions. Memory 708 can include database components, object code components, script components, or any other type of information structure for supporting the various activities and information structures described in the present disclosure. Memory 708 can be communicably connected to processor 706, such as via processing circuit 704, and can include computer code for executing (e.g., by processor 706) one or more processes described herein.

While shown as individual components, it will be appreciated that processor 706 and/or memory 708 can be implemented using a variety of different types and quantities of processors and memory. For example, processor 706 may represent a single processing device or multiple processing devices. Similarly, memory 708 may represent a single memory device or multiple memory devices. Additionally, in some embodiments, controller 702 may be implemented within a single computing device (e.g., one server, one housing, etc.) or multiple devices. For example, the functionality of controller 702 described herein may be implemented across both an implantable device and a remote device that is external to a patient, where the remote device wirelessly communicates with the implantable device and handles a majority of the processing of data. Such an embodiment may reduce the size and/or complexity of controller 702 by reducing the computational load on processing circuit 704 and the components belonging thereto.

Generally, controller 702 (e.g., by processing circuit 704) controls the flow of a fluid (e.g., blood) through tubing 724 by constricting a section of tubing 724 via implantable cuff 722. Specifically, controller 702 may selectively activate or otherwise control a pump 714 to increase hydraulic pressure within implantable cuff 722, which causes a deformable inner wall of implantable cuff 722 to expand inward, towards a central axis of implantable cuff 722. Put another way, the inner wall of implantable cuff 722 may expand from a first diameter to a second diameter, thereby constricting a section of tubing 724 and increasing the resistance of tubing 724 to a fluid flowing therethrough. When pump 714 is subsequently deactivated or reversed, the hydraulic pressure within implantable cuff 722 is reduced, allowing the deformable inner wall of implantable cuff 722 to contract back to the first diameter. Additional details and description of implantable cuff 722 are provided below with respect to FIGS. 9-11.

As shown, pump 714 may be fluidically coupled to implantable cuff 722 via a second tubing 720. Second tubing 720 is generally any flexible, medical-grade tubing, such as PTFE, vinyl, or the like. Pump 714 and second tubing 720 may be permanently or removably coupled; however, it should be appreciated that the coupling between pump 714 and second tubing 720 may be sufficient to withstand the hydraulic pressure applied by pump 714. Similarly, the size and/or material for second tubing 720 may be selected such that the expansion of second tubing 720 due to the activation of pump 714 is minimal or nonexistent. In general, second tubing 720 and implantable cuff 722 are configured to hold (i.e., contain) a predetermine volume of fluid, such as saline. In some embodiments, as discussed in greater detail below, one or both of second tubing 720 and implantable cuff 722 may have a port installed thereon (not shown) that allows a physician or other user to adjust the predetermined amount of fluid.

In some embodiments, pump 714 is a linear actuator; however, pump 714 can generally be any pump that is small enough to be implanted into a patient and that is approved for medical use. Pump 714 may also be a centrifugal pump, a gear pump, a diaphragm pump, a peristaltic pump, or the like, for example. As mentioned above, pump 714 is generally controllable (e.g., by controller 702 or, more specifically, by processing circuit 704) to modulate a pressure of the fluid contained within second tubing 720 and implantable cuff 722, as described in greater detail below. Put another way, pump 714 may increase or decrease the pressure within second tubing 720 and implantable cuff 722, which in turns causes the deformable inner wall of implantable cuff 722 to expand or contract. For example, controller 702 may selectively activate/deactivate pump 714, may adjust a direction of rotation and/or rotation speed of pump 714, or, in the case of a linear actuator, may adjust the extension of the actuator of pump 714. In an embodiment where pump 714 is a linear actuator, for example, activating pump 714 may compress the fluid contained within second tubing 720 and implantable cuff 722, thereby applying hydraulic pressure to the deformable inner wall of implantable cuff 722 and causing implantable cuff 722 to "squeeze" or constrict a section of tubing 724. When pump 714 is deactivated or reversed, the hydraulic pressure applied to the deformable inner wall of implantable cuff 722 may reduce, which correspondingly reduces the amount of constriction to tubing 724.

Still referring to FIG. 7, controller 702 is shown to further include a battery 710 and a corresponding charging circuitry 712. Battery 710 may be any type of rechargeable battery for use in implantable medical devices. For example, battery 710 may be any form of lithium battery (e.g., lithium-ion, lithium iodide-polyvinylpyridine (PVP), lithium silver vanadium oxide (SVO), etc.). Generally, battery 710 may be sized to allow system 700 to operate for a predetermined time period, which may be selected by a physician or other expert. For example, battery 710 may be sized to allow system 700 to operate, without interruption, between visits between the patient and a physician. Charging circuitry 712 may include one or more electrical components for wirelessly charging battery 710 (e.g., via induction). In some embodiments, charging circuitry 712 includes an induction coil and/or rectifier for converting a magnetic field generated by a remote device (e.g., an external charger) into electricity to charge battery 712. In one example, the magnetic field may be generated by an external charger or other device operated by the patient (e.g., in which system 700 is implanted) or a physician. In some embodiments, charging circuitry 712 utilizes resonant inductive charging.

Controller 702 is also shown to include a communications interface 716. Communications interface 716 may facilitate communications between controller and any external components or devices. For example, communications interface 716 can provide means for transmitting data to, or receiving data from, one or more sensors 718 and/or any remote (i.e., external) devices. Accordingly, communications interface 716 can be or can include a wired or wireless communications interface (e.g., jacks, antennas, transmitters, receivers, transceivers, wire terminals, etc.) for conducting data communications. In some embodiments, communications interface 716 may also provide power to various external components. For example, controller 702 may power sensor(s) 718 via communications interface 716. In some embodiments, communications interface 716 includes a wireless transceiver for wirelessly transmitting and receiving data. For example, communications interface 716 may include a WiFi® or Bluetooth® transceiver, or other low-power/short-range wireless transceiver. In this regard, communications interface 716 may provide means for controller 702 to communicate with a remote device, such as a remote programmer operated by a physician (e.g., external to a patient's body). In some embodiments, communications interface 716 may include direct and/or hard-wired communication paths (e.g., wires) for interfacing with sensor(s) 718.

Sensor(s) 718 generally include one or more sensors for measuring various biological/physiological parameters of the patient into which system 700 is implanted. In some embodiments, sensor(s) 718 include one or more electrocardiogram (EKG) sensors that measure electrical signals associated with the patient's heart. In this manner, the patient's cardiac cycle may be recorded to identify different periods or events within the cycle. For example, as described in greater detail below with respect to FIGS. 13 and 14, the diastole and systole periods of the cardiac cycle may be identified such that controller 702 can sync operations of pump 714 to the cardiac cycle. In some embodiments, sensor(s) 718 may include a pulse oximeter or other sensor (s) for determine one or more of the patient's heart rate and blood oxygen level. Using a blood oxygen level measurement, for example, controller 702 may be configured to calculate a measured pulmonary to systemic flow ratio ($Q_p/Q_s$). In some embodiments, controller 702 can then compared the measured $Q_p/Q_s$ to a threshold $Q_p/Q_s$ value or range (e.g., programmed by the physician). If the measured $Q_p/Q_s$ is different from the threshold $Q_p/Q_s$ value and/or outside of a threshold $Q_p/Q_s$ range, then controller 702 may transmit an alert to a remote device (e.g., by wirelessly transmitting an alert to the patient's phone or a physician's computing device) and/or modify control of pump 714 to reach the threshold $Q_p/Q_s$ value or range.

Figure 8:
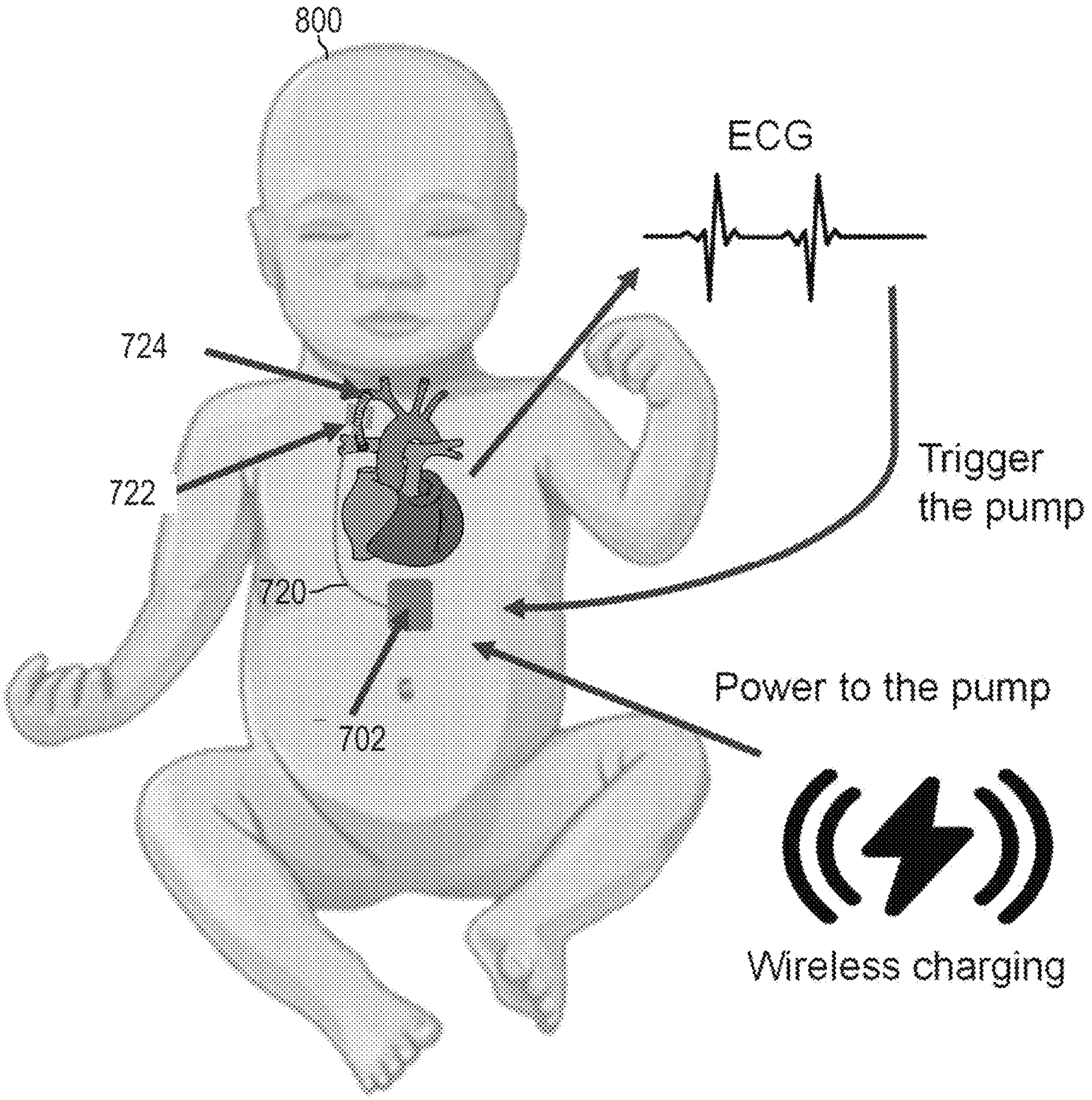
FIG. 8 is a diagram of the active flow control system of FIG. 7 implanted into a patient, according to some embodiments.

Referring now to FIG. 8, a diagram of system 700 implanted into a patient 800 is shown, according to some embodiments. In general, implantable cuff 722 may be positioned on tube 724, which is shown in this example as an atrio-pulmonary or BTTS shunt. Implantable cuff 722 may be fluidically coupled to controller 702 via second tubing 720. Thus, controller 702 may be implanted in any suitable location within the body of patient 800. It should also be appreciated that, in general, controller 702 includes a housing (not shown) and is small enough in size to not be noticed by patient 800 when implanted and/or to limit any discomfort cause by an implantable device.

Figure 9:
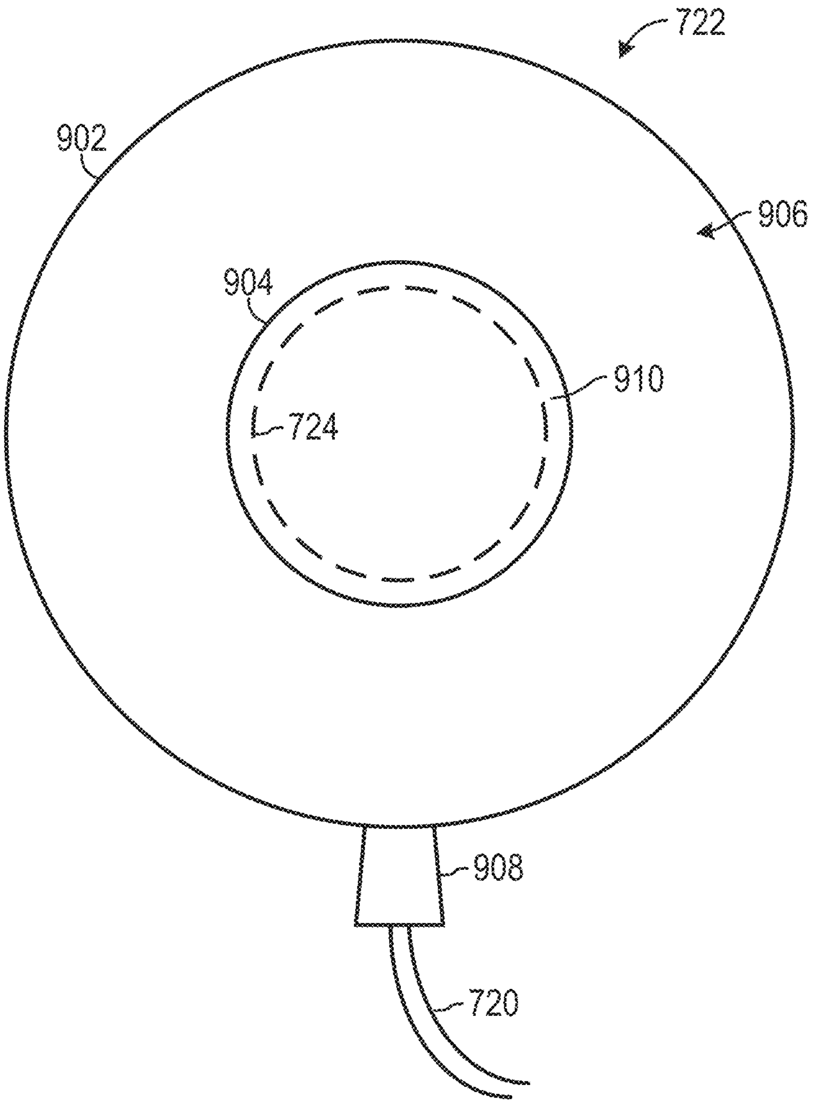
FIG. 9 is a detailed diagram of an implantable cuff of the active flow control system of FIG. 7, according to some embodiments.

Referring now to FIG. 9, a detailed diagram of implantable cuff 722 is shown, according to some embodiments. More specifically, FIG. 9 shows a cross-sectional view of implantable cuff 722. In general, implantable cuff 722 is cylindrical in shape and is formed of an outer wall 902 and an inner wall 904. Each of the outer and inner walls 902, 904 may be formed of any suitable material. For example, outer wall 902 may be formed of a rigid or semi-rigid material (e.g., metal, plastic, etc.) that resists deformation when hydraulic pressure is applied by pump 714. In contrast, inner wall 904 is generally formed of a soft and/or flexible (i.e., deformable) material, such a silicone-based material (e.g., silicone rubber). As shown, outer and inner walls 902, 904 may define an open interior space 906. Implantable cuff 722 is further shown to include a coupling 908 that fluidically couples implantable cuff 722 to second tubing 720.

As shown, a central opening 910 or "channel is formed withing implantable cuff 722, which extends along the central axis of implantable cuff 722, as defined by inner surface 904. Central opening 910 is generally configured/sized to receive tubing 724 therethrough. In FIG. 9, for example, tubing 724 is shown to extend through central opening 910. Put another way, implantable cuff 722 may surround tubing 724, as also shown in greater detail with respect to FIGS. 10 and 11. Thus, when inner wall 904 of implantable cuff 722 expands, the corresponding section of tubing 724 is constricted, which increases the resistance of tubing 724 to the flow of fluid (e.g., blood).

In some embodiments, interior space 906 is filled with a fluid, such as saline. For example, as mentioned above, both second tubing 720 and interior space 906 may be filled with a predetermined amount of fluid. In some embodiments, the amount of fluid is determined by a physician. For example, the physician may determine an amount of saline to fill second tubing 720 and interior space 906 with (e.g., during implantation of system 700) based on the desired amount of constrictive force that inner wall 904 places on tubing 724 when at rest (i.e., when pump 714 is not activated). Thus, the amount of fluid contained within second tubing 720 and interior space 906 may define the initial diameter of inner wall 904 and/or the central opening of implantable cuff 722.

When pump 714 is activated, the limited volume of second tubing 720 and interior space 906 may cause the fluid pressure within second tubing 720 and interior space 906 to increase. In turn, inner wall 904 may deform due it it's elastic/flexible structure. Specifically, the increased hydraulic pressure within interior space 906 causes inner wall 904 to expand toward the central axis of implantable cuff 722 (i.e., to expand into the central opening) which constricts the corresponding portion of tubing 724. In this manner, inner wall 904 may expand inwardly from a first diameter to a second diameter, where the first diameter is larger than the second diameter. When the hydraulic pressure is decreased (e.g., by deactivating and/or reversing pump 714), inner wall 904 may contact back to the first diameter. Additional description of the operation of implantable cuff 722 is provided below with respect to FIG. 12.

Figure 10:
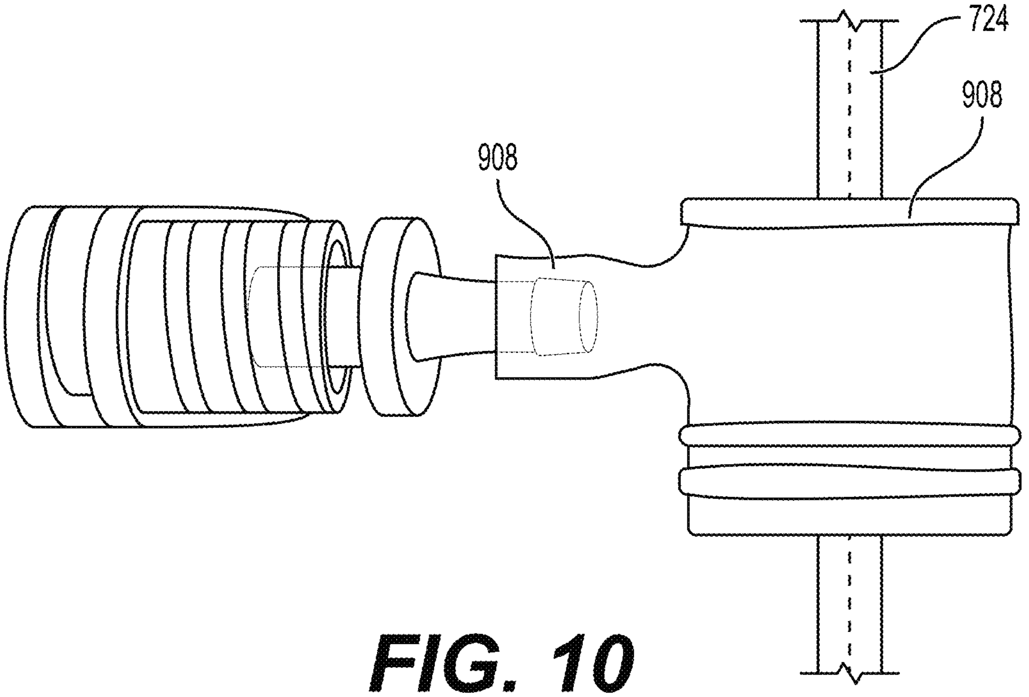
FIGS. 10 and 11 are images of an example implementation of the active flow control system of FIG. 7, according to some embodiments.
Figure 11:
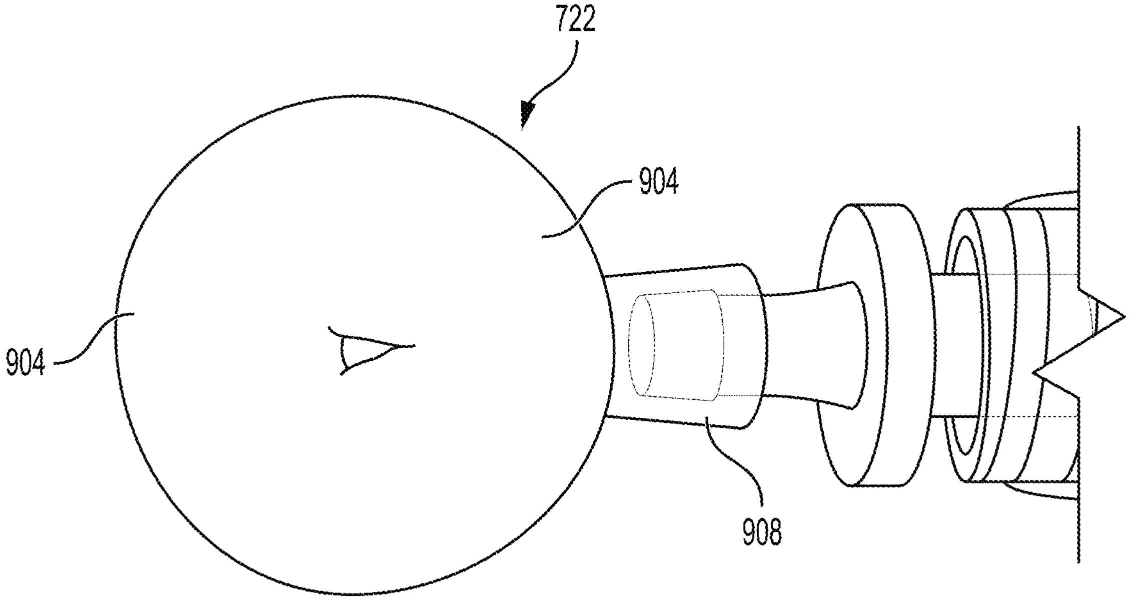

Referring now to FIGS. 10 and 11, images of an example implementation of implantable cuff 722 are shown, according to some embodiments. In FIG. 10, for example, implantable cuff 722 is shown to be positioned on tubing 724. FIG. 10 specifically illustrates the cylindrical shape and size of implantable cuff 722 in a side view. FIG. 11 shows an end-view of implantable cuff 722. Here, the central opening of implantable cuff 722 is clearly shown with tubing 724 removed for clarity. In this example, wall 904 is at least partially expanded into the central opening. Thus, inner wall 904 would be constricting tubing 724.

Figure 12:
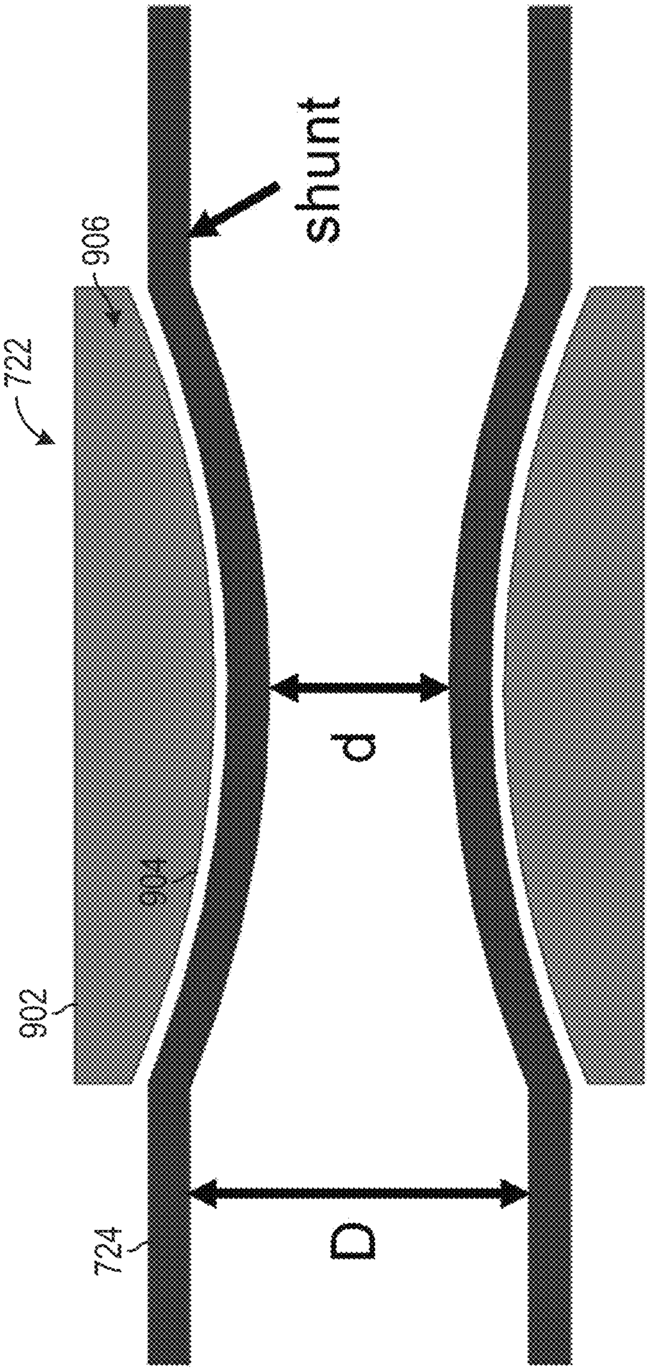
FIG. 12 is a diagram showing a cross-section of an example vessel or tubing having the active flow control system of FIG. 7 positioned thereon, according to some embodiments.

Referring now to FIG. 12, a diagram showing a tubing 724 having implantable cuff 722 positioned thereon is shown, according to some embodiments. Specifically, FIG. 12 is a cut-away, side-view of tubing 724. In this example, tubing 724 is shown to have a diameter, D, with is the internal diameter of tubing 724 in its natural state (i.e., without compression). Implantable cuff 722 is shown to be constricting a portion of tubing 724, thereby reducing the diameter of tubing 724 at a center point of implantable cuff 722 to a diameter, d. As described briefly above, controller 702 may be configured to operate pump 714 to modify cuff-to-tubing diameter ratio, d/D, from 0 (e.g., fully occluded) to 1 (e.g., fully open). For example, as pump 714 increases the pressure within interior space 906 (e.g., by apply hydraulic force to via a fluid), inner wall 904 expands toward the central axis of implantable cuff 722, and thereby tubing 724, reducing d.

Figure 13:
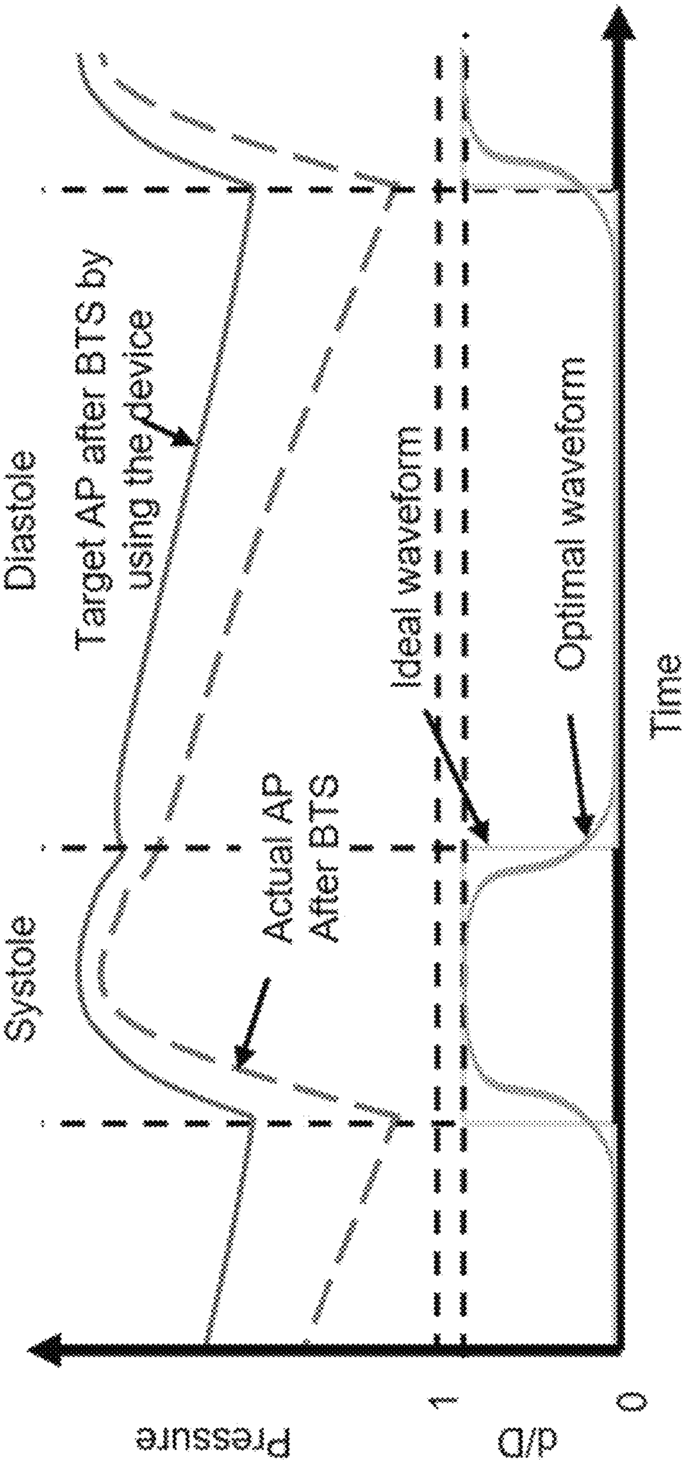
FIG. 13 is a graph showing arterial pressure both with and without the active flow control system of FIG. 7, according to some embodiments.

Referring now to FIG. 13 is a graph showing arterial pressure both with and without system 700, according to some embodiments. Specifically, the graph of FIG. 13 shows actual (i.e., measured) arterial pressure after implantation of a BTTS, represented by a dashed line, along with a target arterial pressure that is achieved using system 700 installed on the BTTS. Additionally, the graph shows a desired d/D ratio curve and an optimized d/D ratio curve over time. It can be seen from the desired d/D ratio curve that controller 702 may activate pump 714 at the start of systole (e.g., for each cardiac cycle) and may deactivate or reverse pump 714 at the end of systole or the start of diastole. In some embodiments, as mentioned above, an initial resistance can be applied to the BTTS or tubing to limit a maximum flow (e.g., shown as the upper horizontal dashed line in FIG. 13) and regulate an appropriate $Q_P/Q_S$. The initial resistance can be set by, for example, a physician, by adjusting the amount of fluid in second tubing 720 and interior space 906. For example, the physician may add fluid (e.g., during or after implantation) to increase the initial resistance within the tubing/BTTS or may remove fluid to decrease the initial resistance within the tubing/BTTS.

Figure 14:
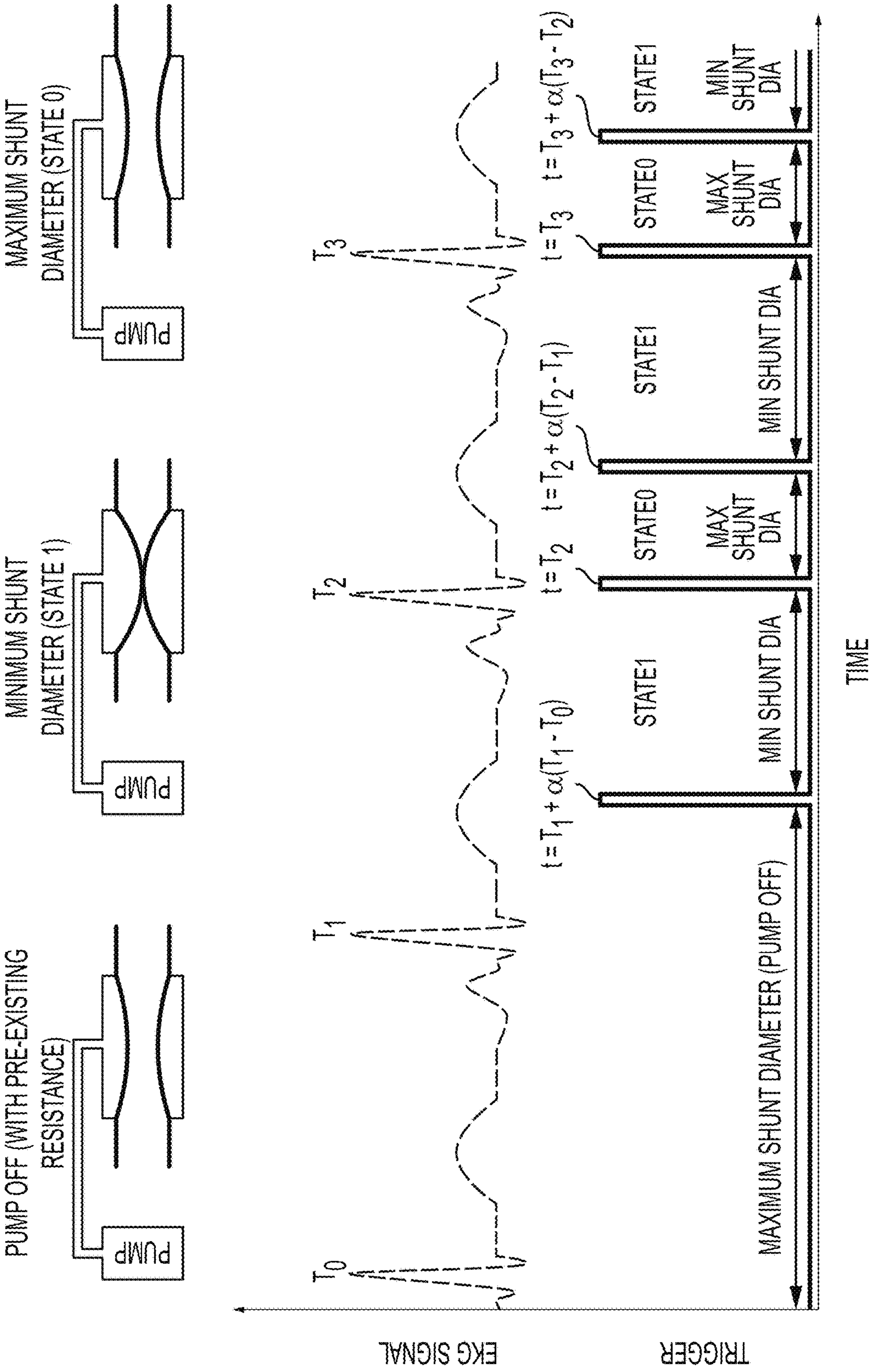
FIG. 14 is a diagram of the trigging process and signals for the active flow control system of FIG. 7, according to some embodiments.

Referring now to FIG. 14 is a diagram of the trigging process and signals for system 700, according to some embodiments. Specifically, FIG. 14 shows a graph of an example EKG signal captured over four cardiac cycles, denoted by starting times $T_0$ to $T_3$. FIG. 14 also illustrates the various operating states of system 700 or, more specifically, implantable cuff 722. For example, at an initial state (State0), a section of tubing 724 (e.g., an atrio-pulmonary shunt) surrounded by implantable cuff 722 is at its maximum diameter. Put another way, the inner wall of implantable cuff 722 is not expanded. As shown, the maximum diameter of the section of tubing 724, and thereby the first diameter of implantable cuff 722, is determined by the amount of fluid in second tubing 720 and interior space 906. When pump 714 is activated (State1), hydraulic pressure causes inner wall 904 of implantable cuff 722 to expand to a second diameter, thereby constricting the section of tubing 724 (i.e., reducing the diameter of the section of tubing 724).

In some embodiments, as mentioned above, system 700 can synchronized to the patient's heartbeat based on recorded EKG signal, as demonstrated by FIG. 14. Specifically, controller 702 may activate (i.e., trigger) pump 714 based on the EKG signal. In some embodiments, controller 702 first determines the when to activate pump 714 by recording a first cardiac cycle, from $T_0$ to $T_1$, and determining a duration of the cycle. In some embodiments, pump 714 is activated at the start of diastole and deactivate or reverse at the start of systole. In some such embodiments, an R-wave from the EKG will be taken and a coefficient for the duration of systole ($\alpha$) assumed as a fraction of the cardiac cycle (e.g., ⅓ of the cardiac cycle) which can be adjusted. As shown, the triggering point for switching pump 714 to State1 (i.e., activating pump 714) can be calculated as:

$$t = T_i + \alpha(T_i - T_{i-1})$$

where t is the triggering time, a is the duration of systole, $T_i$ is the start time of the current cardiac cycle, and $T_{i-1}$ is the start time of the previous cardiac cycle. As shown, pump 714 may then be switched to State0 (i.e., deactivated or reversed) at the start of the next cycle (e.g., $T_{i+1}$).

Figure 15:
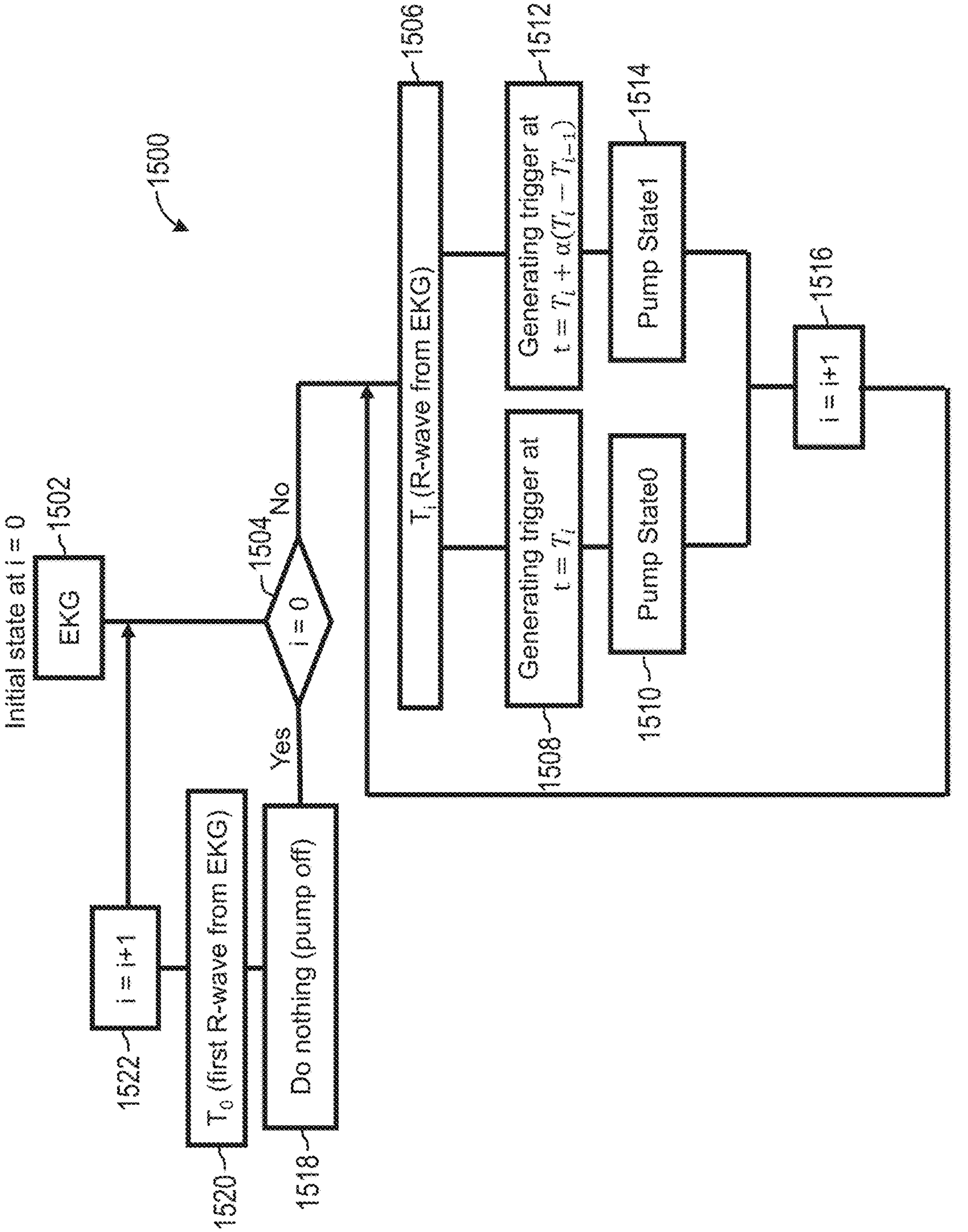
FIGS. 15-18 are flow chart of various processes for controlling the active flow control system of FIG. 7, according to some embodiments.

Referring now to FIGS. 15, a flow chart of a control process 1500 for system 700 is shown, according to some embodiments. In some embodiments, process 1500 is implemented by controller 702, as described above. It will be appreciated that certain steps of process 1500 may be optional and, in some embodiments, process 1500 may be implemented using less than all of the steps. Additionally, while not shown, it should be appreciated that, in some embodiments, the implantation of system 700 and/or a corresponding shunt may proceed process 1500. For example, process 1500 may start with system 700 being provided to, and implanted by, a surgeon or other physician.

At step 1502, an EKG reading is obtained. In some embodiments, the EKG reading is received from a dedicated EKG monitoring device. In other embodiments, the EKG reading is received from an EKG sensor included in system 700 (e.g., sensor 718). It should also be appreciated that, in general, system 700 is in State0 (e.g., pump 714 is not active) at step 1502. In some embodiments, step 1502 also includes setting a counter, i, to an initial value of zero. At step 1504, the counter is evaluated to determine whether i=0. If i is set to zero, indicating that a full cardiac cycle has not been recorded, then process 1500 may continue to step 1518, where pump 714 remains off. At step 1520, the first cardiac cycle is then recorded, and, at step 1522, the counter is increased by 1. As described above, recording the first cardiac cycle allows controller 702 to calculate the start of systole and diastole in subsequent cardiac cycles. Thus, once counter i is greater than 1 (step 1504), process 1500 may continue to step 1506.

At step 1506, controller 702 begins monitoring the EKG signals to detect the start of a cardiac cycle. In this example, the current cardiac cycle is denoted by $T_i$, where i is the value of the counter. At steps 1508 and 1512, triggers are generated when $t=T_i$ and $t=T_i+\alpha(T_i-T_{i-1})$, respectively, as also described above with respect to FIG. 14. When a trigger is generated at step 1508 (e.g., $t=T_i$), pump 714 is deactivated or reversed (e.g., State0). If a trigger is generated at step 1512 (e.g., and $t=T_i+\alpha(T_i-T_{i-1})$), then pump 714 is activated (e.g., State1). Put another way, at the start of the cardiac cycle (e.g., defined by $t=T_i$), pump 714 is inactive or in a default state, where the initial pressure due to the fluid in second tubing 720 and interior space 906 causes implantable cuff 722 to only apply an initial resistance to tubing 724. In contrast, at the start of systole, pump 714 is activate to increase the pressure due to the fluid in second tubing 720 and interior space 906, causing inner wall 904 of implantable cuff 722 to expand and place a constrictive force on a section of tubing 724. Subsequently, at step 1516, counter i is increased by 1. Thus, once a complete cardiac cycle is completed (e.g., $t=T_{i+1}$), steps 1506-1516 of process 1500 may repeat. More specifically, steps 1506-1516 of process 1500 may be continuously executed. In this manner, system 700 may be synced to the patient's heartbeat.

Figure 16:
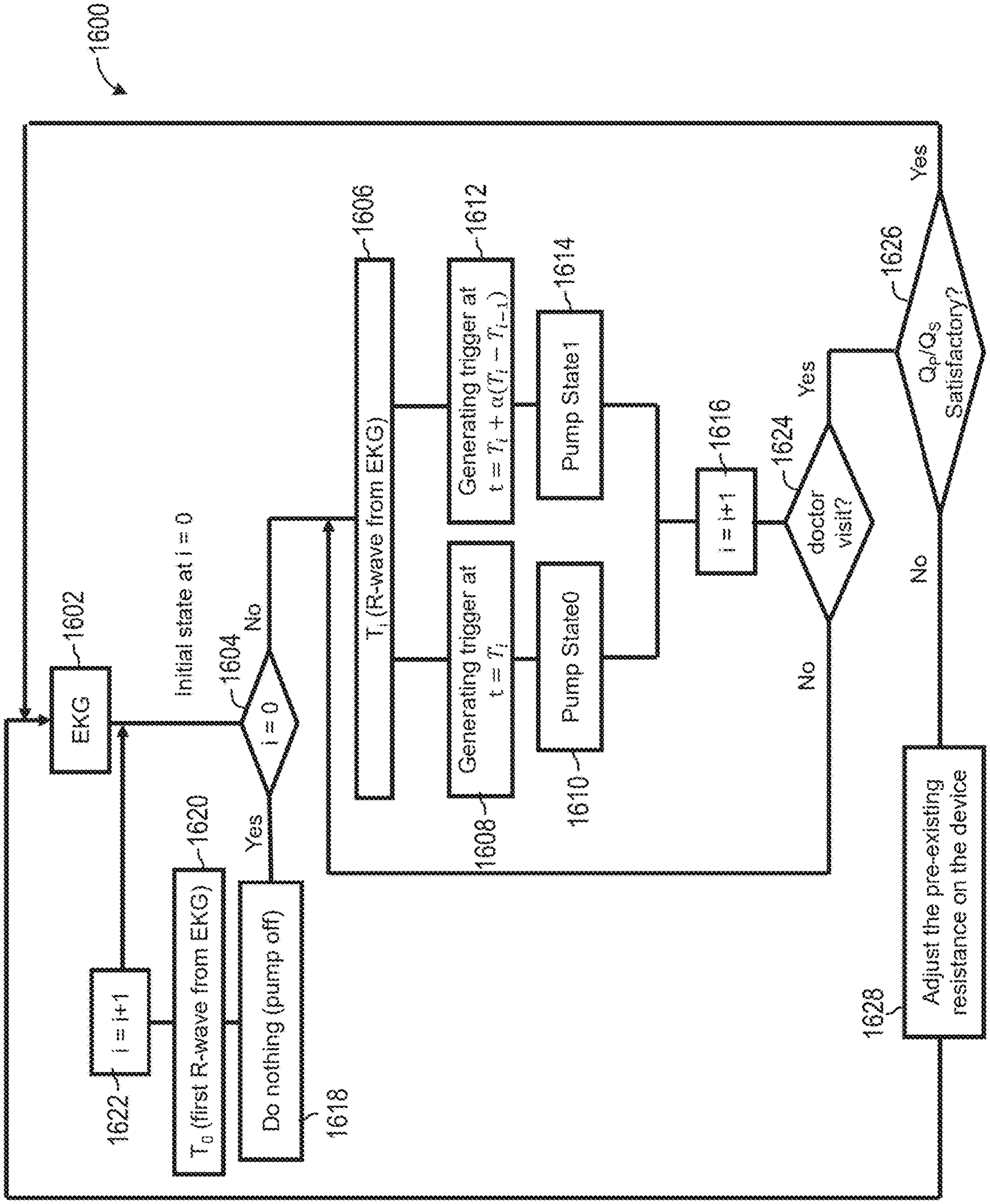

Referring now to FIGS. 16, a flow chart of a control process 1600 for system 700 is shown, according to some embodiments. In some embodiments, process 1600 is implemented by controller 702, as described above. It will be appreciated that certain steps of process 1600 may be optional and, in some embodiments, process 1600 may be implemented using less than all of the steps. In general, steps 1602-1622 of process 1600 may be the same as, or equivalent to, steps 1502-1522 of process 1500, described above. Thus, for the sake of brevity, these steps are not redescribed herein.

Turning instead to step 1624 of process 1600, a determination is made regarding whether or not a visit to a physician is required. In some embodiments, this decision is based on the recorded number of cardiac cycles. In some such embodiments, counter i may be compared to a threshold value and, when i meets or exceeds the threshold, it is determined that the patient should visit a physician. For example, the threshold may be set to two million cycles; thus, when i=2,000,000, process 1600 may continue to step 1626. Otherwise, steps 1606-1624 of process 1600 may continuously repeat.

At step 1626, a determination is made as to whether the $Q_p/Q_s$ value is satisfactory. In some embodiments, the $Q_p/Q_s$ value may be reviewed by a physician to make said determination. If the physician determines that the $Q_p/Q_s$ value is satisfactory (e.g., that the determined $Q_p/Q_s$ value meets a threshold value), then process 1600 may continue to step 1602, where i is reset to zero. Otherwise, if the $Q_p/Q_s$ value is not satisfactory, the physician may adjust the pre-existing or initial resistance provided by implantable cuff 722 to tubing 724. As described above, the pre-existing or initial resistance provided by implantable cuff 722 to tubing 724 is determined by the initial amount of fluid in second tubing 720 and interior space 906. Accordingly, the physician may adjust the pre-existing or initial resistance provided by implantable cuff 722 to tubing 724 by adjusting the amount of fluid in second tubing 720 and interior space 906. For example, removing fluid would decrease the pressure within interior space 906, thereby allowing inner wall 904 of implantable cuff 722 to collapse, reducing the construction on tubing 724. In contrast, adding fluid would increase the pressure within interior space 906, thereby causing inner wall 904 of implantable cuff 722 to expand, increasing the construction on tubing 724. Once the pre-existing or initial resistance is adjusted, process 1600 may continue to step 1602, where i is reset to zero.

Figure 17:
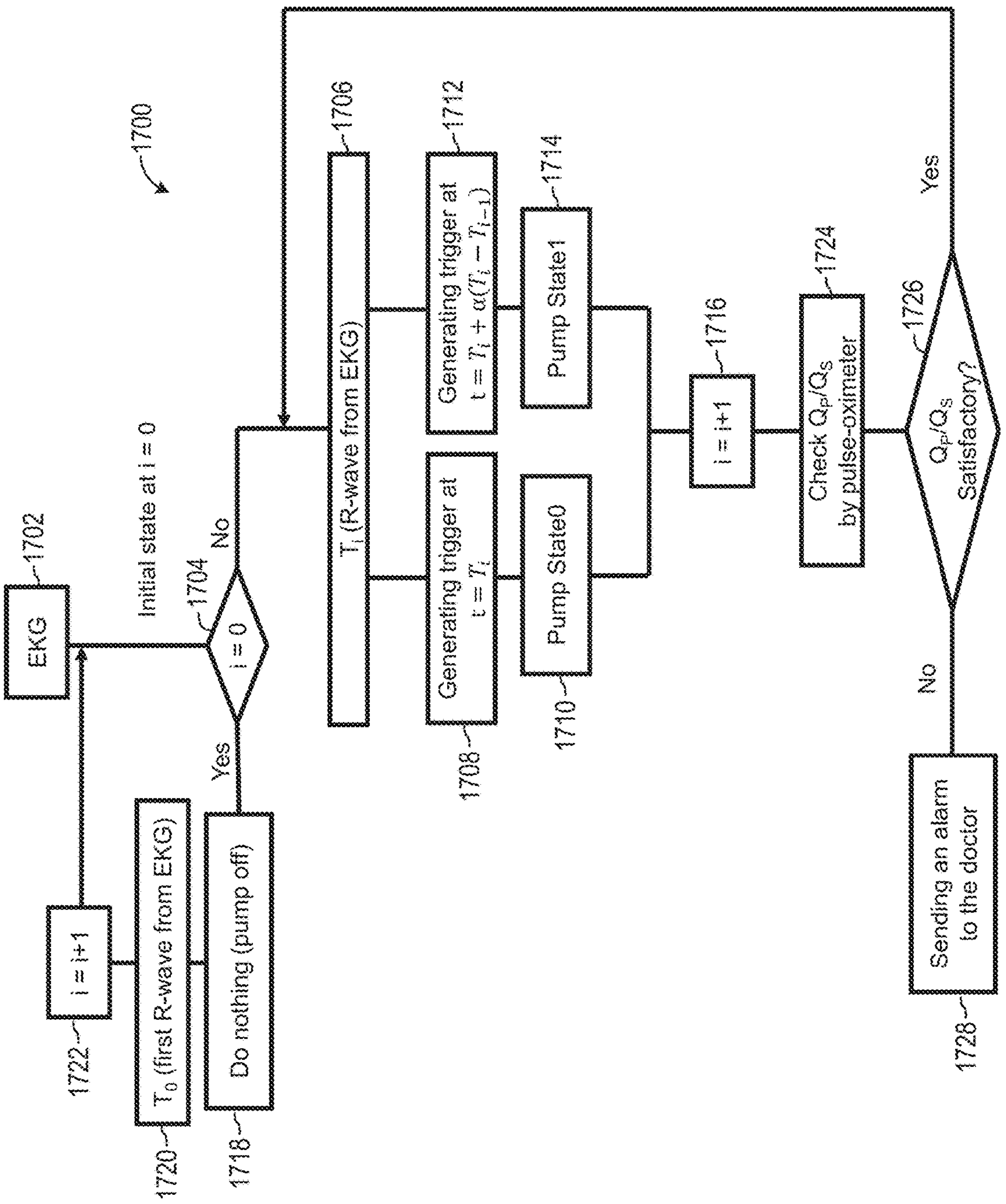

Referring now to FIGS. 17, a flow chart of a control process 1700 for system 700 is shown, according to some embodiments. In some embodiments, process 1700 is implemented by controller 702, as described above. It will be appreciated that certain steps of process 1700 may be optional and, in some embodiments, process 1700 may be implemented using less than all of the steps. In general, steps 1702-1722 of process 1700 may be the same as, or equivalent to, steps 1502-1522 of process 1500, described above. Thus, for the sake of brevity, these steps are not redescribed herein.

Turning instead to step 1724 of process 1700, the $Q_p/Q_s$ value is determined using a pulse-oximeter or readings from a blood oxygen sensor, such as sensor 718. For example, controller 702 may receive sensor data and may calculate the $Q_p/Q_s$ value. If, at step 1726, controller 702 determines that the $Q_p/Q_s$ value is satisfactory (e.g., that the determined $Q_p/Q_s$ value meets a threshold value), then process 1700 may continue to step 1706 such that steps 1706-1726 of process 1700 can be continuously repeated. It should be noted that, in this example, process 1700 does not necessarily return to step 1702 if the $Q_p/Q_s$ value is satisfactory.

Thus, process 1700 allows for the $Q_p/Q_s$ value to be continuously monitored/checked for compliance with predetermined thersholds.

If, at step 1726, the $Q_p/Q_s$ value is not satisfactory, an alarm may be transmitted to a remote device. The remote device may be a device operated by a physician or the patient. For example, controller 702 may wirelessly transmit (e.g., using a short-range transceiver) the alert to a smartphone operated by physician or the patient. In another example, the alarm is transmitted to the patient's device, where it is automatically retransmitted or forwarded to the physician's device. The alarm may indicate to the physician and/or patient that the $Q_p/Q_s$ value is not satisfactory and/or may indicate whether the $Q_p/Q_s$ value is too low or too high. Thus, the physician may adjust the pre-existing or initial resistance provided by implantable cuff 722 to tubing 724, as described above.

Figure 18:
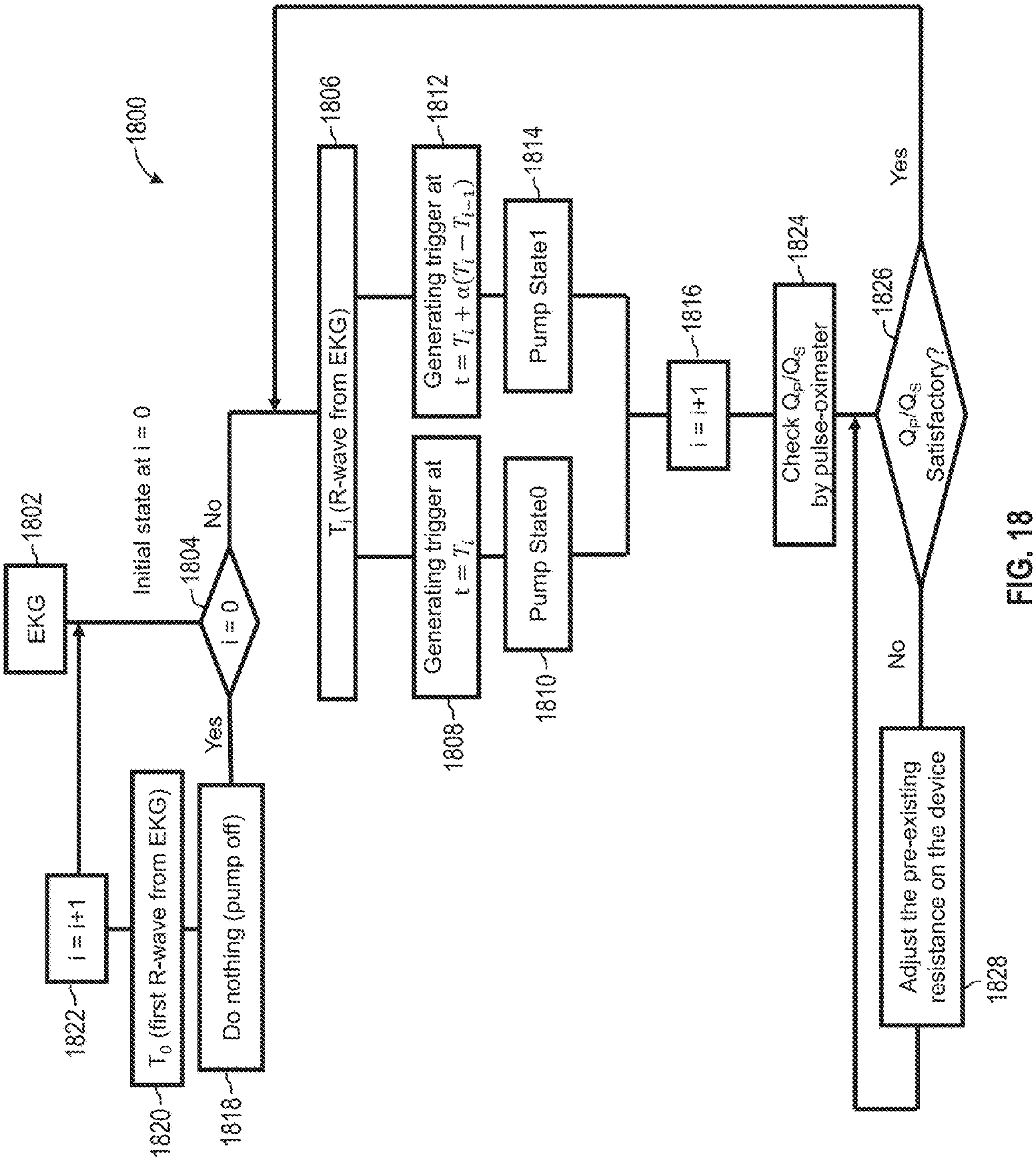

Referring now to FIGS. 18, a flow chart of a control process 1800 for system 700 is shown, according to some embodiments. In some embodiments, process 1800 is implemented by controller 702, as described above. It will be appreciated that certain steps of process 1800 may be optional and, in some embodiments, process 1800 may be implemented using less than all of the steps. In general, steps 1802-1822 of process 1800 may be the same as, or equivalent to, steps 1502-1522 of process 1500, described above. Thus, for the sake of brevity, these steps are not redescribed herein. Additionally, steps 1824 and 1826 of process 1800 are the same as, or equivalent to, steps 1724 and 1726 of process 1700.

However, at step 1828 of process 1800, once it is determined that the $Q_p/Q_s$ value is not satisfactory, controller 702 may automatically adjust the pre-existing or initial resistance provided by implantable cuff 722 to tubing 724. Specifically, rather than adding or removing fluid, controller 702 may adjust the position or operation of pump 714 at the initial state (e.g., State0). For example, controller 702 may cause pump 714 to apply a small amount of pressure to inner wall 904 of implantable cuff 722 even in the initial state, to increase the constriction of the section of tubing 724. If pump 714 is a linear actuator, for example, controller 702 may control the initial or "rest" position of pump 714 to maintain an amount of hydraulic pressure within second tubing 720 and interior space 906. Alternatively, to reduce the initial or pre-existing resistance, controller 702 may control the initial or "rest" position of pump 714 to reduce an amount of hydraulic pressure within second tubing 720 and interior space 906. In some embodiments, steps 1826 and 1828 of process 1800 may continuously repeat until the $Q_p/Q_s$ value is determined to be satisfactory. For example, the position of pump 714 at State0 may be incrementally adjusted and the corresponding $Q_p/Q_s$ value calculated and compared to the threshold.

Figure 19A:
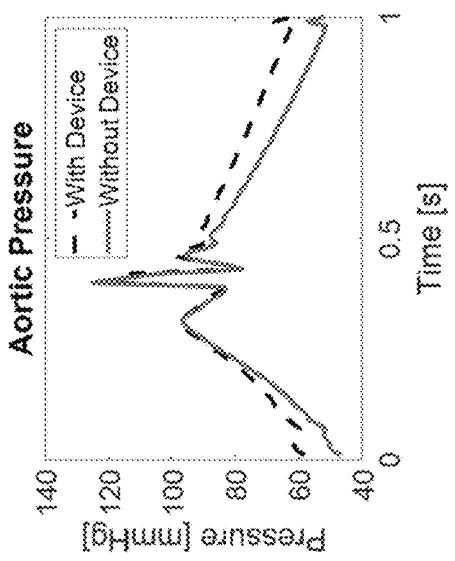
FIGS. 19A-19D are graphs of pressure and flow rate measurements both with and without the active flow control system of FIG. 7, according to some embodiments.
Figure 19B:
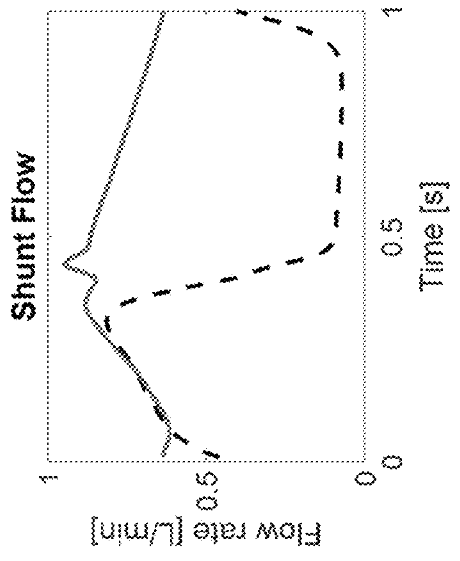
Figure 19C:
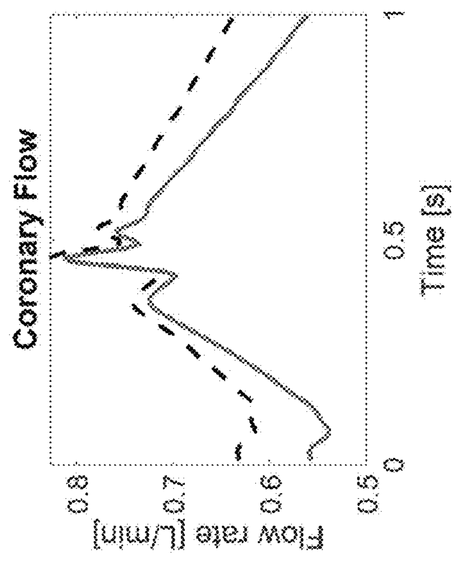
Figure 19D:
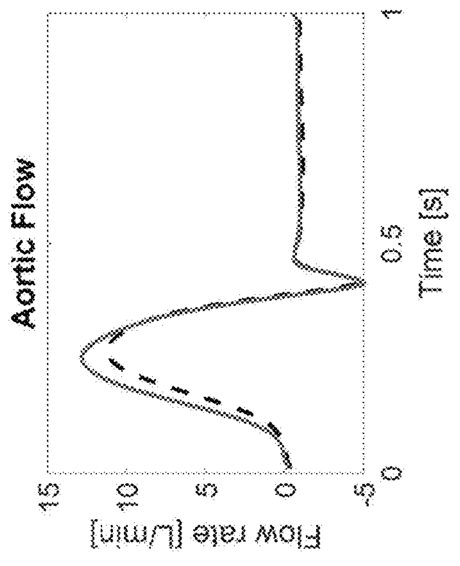

Referring now to FIGS. 19A-19D, various graphs of pressure and flow rate measurements both with and without system 700 installed on an example atrio-pulmonary shunt are shown, according to some embodiments. In FIG. 19A, for example, aortic pressure is shown both with and without system 700 installed on the shunt. FIG. 19C shows the coronary flow rate. FIG. 19D shows the aortic flow rate. Notably, however, FIG. 19B illustrates the flow rate through the shunt, which can be compared to the aortic flow rate of FIG. 19D. It is clearly shown that, without the use of system 700, the shunt flow rate remains high throughout the entire cardiac cycle. However, it would be desirable for the shunt flow to more closely match the aortic flow. Accordingly, it is shown that the addition of system 700 to the shunt causes the shunt flow to more closely match the aortic flow (e.g., by dropping at about 0.3 seconds and remaining low throughout the remainder of the cardiac cycle.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied, and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions, and arrangement of the exemplary embodiments without departing from the scope of the present disclosure.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products including machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures, and which can be accessed by a general purpose or special purpose computer or other machine with a processor.

When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general-purpose computer, special purpose computer, or special purpose processing machines to perform a certain function or group of functions.

Although the figures show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps and decision steps.

It is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

EXEMPLARY ASPECTS

In view of the described processes and compositions, hereinbelow are described certain more particularly described aspects of the disclosures. These particularly recited aspects should not, however, be interpreted to have any limiting effect on any different claims containing different or more general teachings described herein, or that the "particular" aspects are somehow limited in some way other than the inherent meanings of the language and formulas literally used therein.

Example 1: An implantable medical device for controlling a flow of fluid through a tube within a patient, the implantable medical device comprising a first component and a second component movably coupled to one another and defining central passage extending along a central axis of the implantable medical device from a proximal end to a distal end thereof, wherein the central passage is configured for receiving a portion of the tube therethrough, and wherein the first component and the second component each comprise: a proximal clamp portion configured for engaging a proximal portion of the tube; and a distal clamp portion configured for engaging a distal portion of the tube; wherein the implantable medical device is configured for moving between a first configuration and a second configuration, wherein the proximal clamp portions move away from one another and the distal clamp portions move toward one another when the implantable medical device moves from the first configuration to the second configuration.

Example 2: The implantable medical device according to any example herein, particularly example 1, wherein the proximal clamp portions move toward one another and the distal clamp portions move away from one another when the implantable medical device moves from the second configuration to the first configuration.

Example 3: The implantable medical device according to any example herein, particularly example 1 or 2, wherein the implantable medical device is biased to the first configuration.

Example 4: The implantable medical device according to any example herein, particularly example 3, wherein each of the first component and the second component is formed of a shape memory material and has a shape memory corresponding to the first configuration.

Example 5: The implantable medical device according to any example herein, particularly example 3, further comprising a spring that biases the implantable medical device to the first configuration.

Example 6: The implantable medical device according to any example herein, particularly examples 1-5, wherein proximal ends of the proximal clamp portions are spaced apart from one another by a first distance and distal ends of the distal clamp portions are spaced apart from one another by a second distance when the implantable medical device is in the first configuration.

Example 7: The implantable medical device according to any example herein, particularly example 6, wherein the first distance is less than the second distance.

Example 8: The implantable medical device according to any example herein, particularly example 6, wherein the proximal ends of the proximal clamp portions are spaced apart from one another by a third distance and the distal ends of the distal clamp portions are spaced apart from one another by a fourth distance when the implantable medical device is in the second configuration.

Example 9: The implantable medical device according to any example herein, particularly example 8, wherein the third distance is equal to the fourth distance.

Example 10: The implantable medical device according to any example herein, particularly example 8, wherein the third distance is greater than the fourth distance.

Example 11: The implantable medical device according to any example herein, particularly example 8, wherein the implantable medical device is further configured for moving between the second configuration and a third configuration, wherein the proximal clamp portions move away from one another and the distal clamp portions move toward one another when the implantable medical device moves from the second configuration to the third configuration.

Example 12: The implantable medical device according to any example herein, particularly example 11, wherein the proximal ends of the proximal clamp portions are spaced apart from one another by a fifth distance and the distal ends of the distal clamp portions are spaced apart from one another by a sixth distance when the implantable medical device is in the third configuration.

Example 13: The implantable medical device according to any example herein, particularly example 12, wherein the fifth distance is greater than the sixth distance.

Example 14: The implantable medical device according to any example herein, particularly example 12, wherein the proximal clamp portions are configured for constricting the proximal portion of the tube therebetween when the implantable medical device is in the first configuration.

Example 15: The implantable medical device according to any example herein, particularly example 14, wherein the distal clamp portions are configured for not constricting the distal portion of the tube when the implantable medical device is in the first configuration.

Example 16: The implantable medical device according to any example herein, particularly example 15, wherein the proximal clamp portions are configured for constricting the proximal portion of the tube therebetween when the implantable medical device is in the second configuration.

Example 17: The implantable medical device according to any example herein, particularly example 15, wherein the proximal clamp portions are configured for not constricting the proximal portion of the tube therebetween when the implantable medical device is in the second configuration.

Example 18: The implantable medical device according to any example herein, particularly example 15, wherein the distal clamp portions are configured for constricting the distal portion of the tube therebetween when the implantable medical device is in the second configuration.

Example 19: The implantable medical device according to any example herein, particularly example 15, wherein the distal clamp portions are configured for not constricting the distal portion of the tube therebetween when the implantable medical device is in the second configuration.

Example 20: The implantable medical device according to any example herein, particularly example 15, wherein the proximal clamp portions are configured for not constricting the proximal portion of the tube when the implantable medical device is in the third configuration.

Example 21: The implantable medical device according to any example herein, particularly example 20, wherein the distal clamp portions are configured for constricting the distal portion of the tube therebetween when the implantable medical device is in the third configuration.

Example 22: The implantable medical device according to any example herein, particularly example 11, wherein the implantable medical device is configured for moving from the first configuration to the second configuration when a pressure within the proximal portion of the tube exceeds a first pressure threshold.

Example 23: The implantable medical device according to any example herein, particularly example 22, wherein the implantable medical device is configured for moving from the second configuration to the third configuration when the pressure within the proximal portion of the tube exceeds a second pressure threshold that is greater than the first pressure threshold.

Example 24: The implantable medical device according to any example herein, particularly examples 1-23, wherein each of the proximal clamp portions has a partial cylindrical shape, and wherein each of the distal clamp portions has a partial cylindrical shape.

Example 25: The implantable medical device according to any example herein, particularly examples 1-24, wherein each of the proximal clamp portions has a first length, and wherein each of the distal clamp portions has a second length that is different from the first length.

Example 26: The implantable medical device according to any example herein, particularly example 25, wherein the second length is less than the first length.

Example 27: The implantable medical device according to any example herein, particularly example 25, wherein the second length is greater than the first length.

Example 28: The implantable medical device according to any example herein, particularly examples 1-27, wherein an internal surface of each of the proximal clamp portions has a first surface area, and wherein an internal surface of each of the distal clamp portions has a second surface area that is different from the first surface area.

Example 29: The implantable medical device according to any example herein, particularly example 28, wherein the second surface area is less than the first surface area.

Example 30: The implantable medical device according to any example herein, particularly example 28, wherein the second surface area is greater than the first surface area.

Example 31: The implantable medical device according to any example herein, particularly examples 1-30, wherein the first component and the second component are pivotally coupled to one another.

Example 32: The implantable medical device according to any example herein, particularly example 31, wherein the first component and the second component pivot relative to one another when the implantable medical device moves between the first configuration and the second configuration.

Example 33: The implantable medical device according to any example herein, particularly example 31, wherein the first component and the second component are pivotally coupled to one another at a first hinge and a second hinge.

Example 34: The implantable medical device according to any example herein, particularly example 33, wherein the first hinge is disposed along a first side of the implantable medical device, and wherein the second hinge is disposed along an opposite second side of the implantable medical device.

Example 35: The implantable medical device according to any example herein, particularly example 33, wherein the first hinge and the second hinge are disposed opposite one another in a direction perpendicular to the central axis of the implantable medical device.

Example 36: The implantable medical device according to any example herein, particularly example 33, wherein the first hinge and the second hinge are offset from a midpoint between the proximal end and the distal end of the implantable medical device.

Example 37: The implantable medical device according to any example herein, particularly example 33, wherein the first hinge and the second hinge are disposed closer to the proximal end than the distal end of the implantable medical device.

Example 38: The implantable medical device according to any example herein, particularly example 33, wherein the first hinge and the second hinge are disposed closer to the distal end than the proximal end of the implantable medical device.

Example 39: The implantable medical device according to any example herein, particularly example 33, wherein the first component and the second component each further comprise a first hinge portion and a second hinge portion each disposed between the proximal clamp portion and the distal clamp portion, wherein the first hinge portions are pivotally coupled to one another at the first hinge, and wherein the second hinge portions are pivotally coupled to one another at the second hinge.

Example 40: The implantable medical device according to any example herein, particularly example 39, wherein the first hinge portions are pivotally coupled to one another at the first hinge by one or more first fasteners, and wherein the second hinge portions are pivotally coupled to one another at the second hinge by one or more second fasteners.

Example 41: The implantable medical device according to any example herein, particularly example 39, wherein the first component and the second component each further comprise an intermediate portion extending from the proximal clamp portion to the distal clamp portion, and wherein the first hinge portion and the second hinge portion each extend from the intermediate portion.

Example 42: The implantable medical device according to any example herein, particularly example 41, wherein, for each of the first component and the second component, the proximal clamp portion, the distal clamp portion, the intermediate portion, the first hinge portion, and the second hinge portion are integrally formed within one another.

Example 43: The implantable medical device according to any example herein, particularly examples 1-42, wherein the tube is a vessel of the patient.

Example 44: The implantable medical device according to any example herein, particularly examples 1-43, wherein the tube is a formed of a biocompatible synthetic material.

Example 45: The implantable medical device according to any example herein, particularly examples 1-44, wherein the tube is a shunt.

Example 46: The implantable medical device according to any example herein, particularly examples 1-45, wherein the tube is an atrio-pulmonary shunt.

Example 47: The implantable medical device according to any example herein, particularly examples 1-46, wherein the tube is a modified Blalock-Tausig shunt or a Blalock-Thomas-Taussig shunt (BTTS).

Example 48: The implantable medical device according to any example herein, particularly examples 1-47, further comprising the tube.

Example 49: The implantable medical device according to any example herein, particularly examples 1-48, wherein the first component and the second component extend around the tube such that the proximal clamp portions and the distal clamp portions engage an external surface of the tube.

Example 50: The implantable medical device according to any example herein, particularly examples 1-49, wherein the first component and the second component are embedded within a wall of the tube such that the first component and the second component are disposed between an external surface and an internal surface of the tube.

Example 51: A method of using an implantable medical device for controlling a flow of fluid through a tube within a patient, the method comprising engaging a proximal portion of the tube with a plurality of proximal clamp portions of the implantable medical device; engaging a distal portion of the tube with a plurality of distal clamp portions of the implantable medical device; and allowing the implantable medical device to move between a first configuration and a second configuration, wherein the proximal clamp portions move away from one another and the distal clamp portions move toward one another when the implantable medical device moves from the first configuration to the second configuration.

Example 52: The method according to any example herein, particularly example 51, wherein the proximal clamp portions move toward one another and the distal clamp portions move away from one another when the implantable medical device moves from the second configuration to the first configuration.

Example 53: The method according to any example herein, particularly example 51 or 52, wherein the implantable medical device is biased to the first configuration.

Example 54: The method according to any example herein, particularly examples 51-53, wherein the proximal clamp portions constrict the proximal portion of the tube therebetween when the implantable medical device is in the first configuration, thereby restricting the flow of fluid through the tube.

Example 55: The method according to any example herein, particularly example 54, wherein the distal clamp portions do not constrict the distal portion of the tube therebetween when the implantable medical device is in the first configuration.

Example 56: The method according to any example herein, particularly example 54, wherein the proximal clamp portions constrict the proximal portion of the tube therebetween when the implantable medical device is in the second configuration, thereby restricting the flow of fluid through the tube.

Example 57: The method according to any example herein, particularly example 54, wherein the proximal clamp portions do not constrict the proximal portion of the tube therebetween when the implantable medical device is in the second configuration.

Example 58: The method according to any example herein, particularly example 54, wherein the distal clamp portions constrict the distal portion of the tube therebetween when the implantable medical device is in the second configuration, thereby restricting the flow of fluid through the tube.

Example 59: The method according to any example herein, particularly example 54, wherein the distal clamp portions do not constrict the distal portion of the tube therebetween when the implantable medical device is in the second configuration.

Example 60: The method according to any example herein, particularly example 54, further comprising allowing the implantable medical device to move between the second configuration and a third configuration, wherein the proximal clamp portions move away from one another and the distal clamp portions move toward one another when the implantable medical device moves from the second configuration to the third configuration.

Example 61: The method according to any example herein, particularly example 60, wherein the distal clamp portions constrict the distal portion of the tube therebetween when the implantable medical device is in the third configuration, thereby restricting the flow of fluid through the tube.

Example 62: The method according to any example herein, particularly example 61, wherein the proximal clamp portions do not constrict the proximal portion of the tube therebetween when the implantable medical device is in the third configuration.

Example 63: The method according to any example herein, particularly example 60, further comprising causing the implantable medical device to move from the first configuration to the second configuration when a pressure within the proximal portion of the tube exceeds a first pressure threshold.

Example 64: The method according to any example herein, particularly example 63, further comprising causing the implantable medical device to move from the second configuration to the third configuration when the pressure within the proximal portion of the tube exceeds a second pressure threshold that is greater than the first pressure threshold.

Example 65: The method according to any example herein, particularly examples 51-64, wherein the flow of fluid is a flow of blood.

Example 66: The method according to any example herein, particularly examples 51-65, wherein the tube is a vessel of the patient.

Example 67: The method according to any example herein, particularly examples 51-66, wherein the tube is a formed of a biocompatible synthetic material.

Example 68: The method according to any example herein, particularly examples 51-67, wherein the tube is a shunt.

Example 69: The method according to any example herein, particularly examples 51-68, wherein the tube is an atrio-pulmonary shunt.

Example 70: The method according to any example herein, particularly examples 51-69, wherein the tube is a modified Blalock-Tausig shunt or a Blalock-Thomas-Taussig shunt (BTTS).

Example 71: An implantable medical device for controlling a flow of a first fluid through a tubing, the implantable medical device comprising a flow control cuff comprising a stiff outer wall and a deformable inner wall which defines a central opening that extends along a central axis of the flow control cuff, wherein the central opening is sized such that the tubing can extend therethrough, and wherein the stiff outer wall and the deformable inner wall form an interior space that is filled with a second fluid; a pump configured to modulate a pressure of the second fluid within the interior space, wherein the deformable inner wall expands toward the central axis when the pressure of the second fluid is increased to apply a constrictive force to a section of the tubing; and a controller configured to control the flow of the first fluid through the tubing by selectively activating the pump to temporarily increase the pressure of the second fluid in the interior space, thereby selectively expanding the deformable inner wall of the flow control cuff.

Example 72: The implantable medical device according to any example herein, particularly example 71, wherein the tubing is a Blalock-Tausig shunt or a Blalock-Thomas-Taussig shunt (BTTS).

Example 73: The implantable medical device according to any example herein, particularly example 71 or 72, wherein the second fluid is saline.

Example 74: The implantable medical device according to any example herein, particularly examples 71-73, wherein the deformable inner wall is formed of a silicone-based material.

Example 75: The implantable medical device according to any example herein, particularly examples 71-74, wherein the pump is a linear actuator.

Example 76: The implantable medical device according to any example herein, particularly examples 71-75, further comprising a wirelessly rechargeable battery.

Example 77: The implantable medical device according to any example herein, particularly examples 71-76, further comprising a wireless transceiver for wirelessly transmitting and receiving data from a remote device.

Example 78: The implantable medical device according to any example herein, particularly examples 71-77, further comprising a sensor for measuring EKG signals indicative of a cardiac cycle, wherein the controller is further configured to selectively activate the pump based on the cardiac cycle.

Example 79: The implantable medical device according to any example herein, particularly example 78, wherein the controller activates the pump to expand the deformable inner wall of the flow control device at a start of diastole and deactivates or reverses the pump to collapse the deformable inner wall of the flow control device at a start of systole.

Example 80: The implantable medical device according to any example herein, particularly examples 71-79, wherein the first fluid is blood, the implantable medical device further comprising a sensor for measuring an oxygen saturation of the blood.

Example 81: The implantable medical device according to any example herein, particularly example 80, wherein the controller is further configured to determine a pulmonary to systemic flow ratio ($Q_P/Q_S$) based on measurements from the sensor; compare the determined $Q_P/Q_S$ to a threshold $Q_P/Q_S$; and either transmit an alert to a remote device indicating the determined $Q_P/Q_S$ is not satisfactory or automatically adjust the pressure of the second fluid until the determined $Q_P/Q_S$ meets the threshold $Q_P/Q_S$.

Example 82: The implantable medical device according to any example herein, particularly examples 71-81, wherein the second fluid has an initial pressure that can be modified by a physician to adjust a diameter of the central opening when the pump is not active.

Example 83: The implantable medical device according to any example herein, particularly examples 71-82, wherein activating, by the controller, the pump causes the deformable inner wall of the flow control cuff to expand from a first diameter to a second diameter.

Example 84: The implantable medical device according to any example herein, particularly example 83, wherein the central opening is larger when the deformable inner wall of the flow control cuff is at the first diameter than the second diameter.

Example 85: A method comprising providing a flow control device to be implanted on an atrio-pulmonary shunt in a patient, the flow control device comprising an implantable flow control cuff having a stiff outer wall and a deformable inner wall which defines a central opening that extends along a central axis of the flow control cuff, wherein the central opening is sized such that the atrio-pulmonary shunt can extend therethrough, and wherein the stiff outer wall and the deformable inner wall for an interior space is filled with a fluid; recording, by a controller, electrocardiogram (EKG) signals to detect timing of diastole and systole in a patient's cardiac cycle; and based on the timing of diastole and systole in the patient's cardiac cycle: activating, by the controller, a pump to increase a pressure of the fluid within the interior space responsive to the cardiac cycle entering a diastole period, wherein the increase in the pressure causes the deformable inner wall of the implantable flow control cuff to expand from a first diameter to second diameter to apply a constrictive force to a section of the atrio-pulmonary shunt; or deactivating or reversing, by the controller, the pump to decrease the pressure of the fluid within the interior space responsive to the cardiac cycle entering a systole period, wherein the decrease in the pressure causes the deformable inner wall of the implantable flow control cuff to contract from the second diameter to the first diameter to remove the constrictive force to the section of the atrio-pulmonary shunt.

Example 86: The method according to any example herein, particularly example 85, wherein the atrio-pulmonary shunt is a modified Blalock-Tausig shunt or a Blalock-Thomas-Taussig shunt (BTTS).

Example 87: The method according to any example herein, particularly example 85 or 86, wherein the fluid is saline.

Example 88: The method according to any example herein, particularly examples 85-87, wherein the deformable inner wall is formed of a silicone-based material.

Example 89: The method according to any example herein, particularly examples 85-88, wherein the pump is a linear actuator.

Example 90: The method according to any example herein, particularly examples 85-89, further comprising measuring, by the controller, an oxygen saturation of the blood.

Example 91: The method according to any example herein, particularly example 90, further comprising determining, by the controller, a pulmonary to systemic flow ratio ($Q_P/Q_s$) based on the measured oxygen saturation; comparing, by the controller, the determined $Q_P/Q_s$ to a threshold $Q_P/Q_s$; and either transmitting, by the controller, an alert to a remote device indicating the determined $Q_P/Q_s$ is not satisfactory or automatically adjusting, by the controller, the pressure of the fluid until the determined $Q_P/Q_s$ meets the threshold $Q_P/Q_s$.

Example 92: The method according to any example herein, particularly examples 85-91, wherein the fluid has an initial pressure that can be modified by a physician to adjust the first diameter.

Example 93: The method according to any example herein, particularly examples 85-92, wherein the controller and the pump are implantable.

Example 94: A system comprising an implantable cuff comprising a stiff outer wall and a deformable inner wall which defines a central opening that extends along a central axis of the implantable cuff, wherein the central opening is sized such that an atrio-pulmonary shunt can extend therethrough, and wherein the stiff outer wall and the deformable inner wall for an interior space is filled with a fluid; a pump configured to modulate a pressure of the fluid within the interior space to selectively expand the deformable inner wall from a first diameter to a second diameter, wherein the first diameter is larger than the second diameter such that the deformable inner wall expands toward the central axis to apply a constrictive force to a section of the atrio-pulmonary shunt when the deformable inner wall is expanded to the second diameter; and a controller configured to control flow of the fluid through the atrio-pulmonary shunt by selectively activating the pump to cause the deformable inner wall to expand from the first diameter to the second diameter or contract from the second diameter to the first diameter.

Example 95: The system according to any example herein, particularly example 94, wherein the atrio-pulmonary shunt is a modified Blalock-Tausig shunt or a Blalock-Thomas-Taussig shunt (BTTS).

Example 96: The system according to any example herein, particularly example 94 or 95, wherein the fluid is saline.

Example 97: The system according to any example herein, particularly examples 94-96, wherein the deformable inner wall is formed of a silicone-based material.

Example 98: The system according to any example herein, particularly examples 94-97, wherein the pump is a linear actuator.

Example 99: The system according to any example herein, particularly examples 94-98, further comprising a wirelessly rechargeable battery.

Example 100: The system according to any example herein, particularly examples 94-99, further comprising a wireless transceiver for wirelessly transmitting and receiving data from a remote device.

Example 101: The system according to any example herein, particularly examples 94-100, further comprising a sensor for measuring EKG signals indicative of a cardiac cycle, wherein the controller is further configured to selectively activate the pump based on the cardiac cycle.

Example 102: The system according to any example herein, particularly example 101, wherein the controller is configured to activate the pump to expand the deformable inner wall of the implantable cuff from the first diameter to the second diameter at a start of diastole; and deactivate or reverse the pump to collapse the deformable inner wall of the implantable cuff from the second diameter to the first diameter at a start of systole.

Example 103: The system according to any example herein, particularly examples 94-102, further comprising a sensor for measuring an oxygen saturation of the blood.

Example 104: The system according to any example herein, particularly example 103, wherein the controller is further configured to determine a pulmonary to systemic flow ratio ($Q_P/Q_s$) based on measurements from the sensor; compare the determined $Q_P/Q_s$ to a threshold $Q_P/Q_s$; and either transmit an alert to a remote device indicating the determined $Q_P/Q_s$ is not satisfactory or automatically adjust the pressure of the fluid until the determined $Q_P/Q_s$ meets the threshold $Q_P/Q_s$.

Example 105: The system according to any example herein, particularly examples 94-104, wherein the fluid has an initial pressure that can be modified by a physician to adjust the first diameter.

What is claimed is:

1. An implantable medical device for controlling a flow of fluid through a tube within a patient, the implantable medical device comprising:

a first component and a second component movably coupled to one another and defining a central passage extending along a central axis of the implantable medical device from a proximal end to a distal end thereof, wherein the central passage is configured for receiving a portion of the tube therethrough, wherein the first component and the second component comprise, respectively, (i) a first elongate straight structure having a first proximal clamp portion at the proximal end configured for engaging a proximal portion of the tube and a first distal clamp portion at the distal end configured for engaging a distal portion of the tube, and (ii) a second elongate straight structure having a second proximal clamp portion at the proximal end configured for engaging the proximal portion of the tube and a second distal clamp portion at the distal end configured for engaging the distal portion of the tube, the first elongate straight structure and the second elongate straight structure being disposed opposite one another in a direction of the central axis and include a pivotal coupling to move between a first configuration and a second configuration by movement of the first component and the second component, and wherein the proximal clamp portions move away from one another and the distal clamp portions move toward one another when the implantable medical device moves at the pivotal coupling from the first configuration to the second configuration.

2. The implantable medical device of claim 1, wherein the first and second proximal clamp portions move toward one another and the first and second distal clamp portions move away from one another when the implantable medical device moves from the second configuration to the first configuration.

3. The implantable medical device of claim 1, wherein the implantable medical device is biased to the first configuration.

4. The implantable medical device of claim 3, wherein each of the first component and the second component is formed of a shape memory material and has a shape memory corresponding to the first configuration.

5. The implantable medical device of claim 3, further comprising a spring that biases the implantable medical device to the first configuration.

6. The implantable medical device claim 1, wherein proximal ends of the first and second proximal clamp portions are spaced apart from one another by a first distance and distal ends of the first and second distal clamp portions are spaced apart from one another by a second distance when the implantable medical device is in the first configuration, and wherein the proximal ends of the first and second proximal clamp portions are spaced apart from one another by a third distance and the distal ends of the first and second distal clamp portions are spaced apart from one another by a fourth distance when the implantable medical device is in the second configuration.

7. The implantable medical device of claim 6, wherein the implantable medical device is further configured for moving between the second configuration and a third configuration, wherein the first and second proximal clamp portions move away from one another and the first and second distal clamp portions move toward one another when the implantable medical device moves from the second configuration to the third configuration.

8. The implantable medical device of claim 6, wherein the first and second proximal clamp portions are configured for constricting the proximal portion of the tube therebetween when the implantable medical device is in the first configuration, and wherein the first and second distal clamp portions are configured for not constricting the distal portion of the tube when the implantable medical device is in the first configuration.

9. The implantable medical device of claim 6, wherein the first and second proximal clamp portions are configured for constricting the proximal portion of the tube therebetween when the implantable medical device is in the second configuration.

10. The implantable medical device of claim 6, wherein the first and second proximal clamp portions are configured for not constricting the proximal portion of the tube therebetween when the implantable medical device is in the second configuration.

11. The implantable medical device of claim 1, wherein the implantable medical device is configured for moving from the first configuration to the second configuration when a pressure within the proximal portion of the tube exceeds a first pressure threshold.

12. The implantable medical device of claim 1, wherein each of the first and second proximal clamp portions has a partial cylindrical shape, and wherein each of the first and second distal clamp portions has a partial cylindrical shape.

13. The implantable medical device of claim 1, wherein each of the first and second proximal clamp portions has a first length, and wherein each of the first and second distal clamp portions has a second length that is different from the first length.

14. The implantable medical device of claim 1, wherein an internal surface of each of the first and second proximal clamp portions has a first surface area, and wherein an internal surface of each of the first and second distal clamp portions has a second surface area that is different from the first surface area.

15. The implantable medical device of claim 1, wherein the first component and the second component are pivotally coupled to one another, wherein the first component and the second component pivot relative to one another when the implantable medical device moves between the first configuration and the second configuration.

16. The implantable medical device of claim 1, wherein the tube is one of a vessel of the patient, an atrio-pulmonary shunt, a modified Blalock-Tausig shunt, or a Blalock-Thomas-Taussig shunt (BTTS).

17. The implantable medical device of claim 1, wherein the first component and the second component extend around the tube such that the first and second proximal clamp portions and the first and second distal clamp portions engage an external surface of the tube.

18. The implantable medical device of claim 1, wherein the first component and the second component are embedded within a wall of the tube such that the first component and the second component are disposed between an external surface and an internal surface of the tube.

* * * * *